US00RE38352E

(19) United States
(12) Reissued Patent
Kozal et al.

(10) Patent Number: US RE38,352 E
(45) Date of Reissued Patent: *Dec. 16, 2003

(54) POLYMERASE CHAIN REACTION ASSAYS FOR MONITORING ANTIVIRAL THERAPY AND MAKING THERAPEUTIC DECISIONS IN THE TREATMENT OF ACQUIRED IMMUNODEFICIENCY SYNDROME

(75) Inventors: Michael J. Kozal, Menlo Park, CA (US); Thomas C. Merigan, Portola Valley, CA (US)

(73) Assignee: Leland Stanford Junior University, Palo Alto, CA (US)

( * ) Notice: This patent is subject to a terminal disclaimer.

(21) Appl. No.: 10/236,326

(22) Filed: Sep. 5, 2002

Related U.S. Patent Documents

Reissue of:

(64) Patent No.: 5,856,086
Issued: Jan. 5, 1999
Appl. No.: 08/783,786
Filed: Jan. 15, 1997

U.S. Applications:

(63) Continuation of application No. 08/290,311, filed on Aug. 15, 1994, now Pat. No. 5,631,128, which is a continuation-in-part of application No. 07/883,327, filed on May 14, 1992, now abandoned.

(51) Int. Cl.[7] ..... C12Q 1/70; C12Q 1/68; C12P 19/34; C07H 21/04

(52) U.S. Cl. ..... 435/5; 435/6; 435/91.1; 435/91.2; 435/91.51; 536/23.1; 536/24.3; 536/211.31; 536/24.32; 536/24.33; 514/2; 514/44; 514/45; 436/63; 436/501; 436/601

(58) Field of Search ..... 435/5, 6, 91.1, 435/91.2, 91.51, 974; 436/63, 501, 601; 514/2, 44, 45; 536/23.1, 24.3, 24.31, 24.32, 24.33; 935/77, 78

(56) References Cited

U.S. PATENT DOCUMENTS

| | | | | |
|---|---|---|---|---|
| 4,683,195 | A | 7/1987 | Mullis et al. | 435/6 |
| 5,008,182 | A | 4/1991 | Sninsky et al. | |
| 5,409,810 | A | 4/1995 | Lander et al. | 435/5 |
| 5,631,128 | A | 5/1997 | Kozal et al. | 435/5 |
| 5,650,268 | A | 7/1997 | Kozal et al. | 435/5 |

FOREIGN PATENT DOCUMENTS

| | | |
|---|---|---|
| EP | 0229709 | 7/1987 |
| EP | 0-422-762 A2 | 8/1990 |
| GB | A-60828/90 | 7/1987 |

OTHER PUBLICATIONS

Singer et al., "Clinical significance of in vitro HIV resistance to zidovudine in early HIV infected individuals after 4 years of therapy", Int. Conf. AIDS 7(2): 285 (Abstract only W.B. 2414).

Boucher, et al., (1992) "Ordered Appearance of Zidovudine Resistance Mutations During Treatment of 18 Human Immunodefiency Virus–Positive Subjects," *J. Infect. Dis.,* 165:105–110.

Bush, et al., (1992) "Detection of Human Immunodeficiency Virus Type 1 RNA in Plasma Samples from High–Risk Pediatric Patients by Using the Self–Sustained Sequence Replication Reaction," *J. Clin. Microbiology,* 30(2):281–286.

Chomczynski, et al., (1987) "Single–Step method of RNA Isolation by Acid Guanidinium Thiocyanate–Phenol–Chloroform Extraction," *Anal. Biochem.* 162:156–159.

Coombs, et al., (1989) "Plasma Viremia in Human Immunodeficiency Virus Infection," *N. Eng. J. Med.,* 321:1626–31.

Coyle, et al., (1990) "Detection of Human Immunodeficiency Virus in Plasma by RNA Directed Polymerase Chain Reaction in a Cohort of Hemophiliacs," *Clin. Res.* 38:778a (Abstr.).

Daar, et al., (1991) "Transient High Levels of Viremia in Patients with Primary Human Immunodeficiency Virus Type 1 Infection," *N. Engl. J. Med.,* 324:961–964.

Ehrnst, et al., (1988) "Efficient Isolation of HIV From Plasma During Different Stages of HIV Infection," *J. Med. Virol.,* 26:23–32.

Eron, et al., (1993) "Pol mutations conferring zidovudine and didanosine resistance with different effects in vitro yield multiply resistant human immunodeficiency virus type 1 isolates in vivo," *Antimicrob. Agents Chemother.,* 37:1480–7.

Eron, et al., (1992) "Susceptibility testing by polymerase chain DNA quantitation: A method to measure drug resistance of human immunodeficiency virus type 1 isolates," *Proc. Natl. Acad. Sci.* 89:3241–3245.

Escaich, et al., (1991) "Plasma Viraemia as a Marker of Viral Replication in HIV–Infected Individuals," *Aids,* 5:1189–1193.

Fischel, et al., (1990) "A Randomized Controlled Trial of a Reduced Daily Dose of Zidovudine in Patients with the Acquired Immunodeficiency Syndrome," *N. Engl. J. Med,* 323:1009–1014.

Gu Z, et al., "Novel mutation in the human immunodeficiency virus type 1 reverse transcriptase gene that encodes cross–resistance in 2'3'–dideoxyinosine and 2'3'–dideoxycytidine," *J. Virol.,* 66:7128–35.

(List continued on next page.)

*Primary Examiner*—Jeffrey Fredman
(74) *Attorney, Agent, or Firm*—Glenn W. Rhodes; Karen K. Wong; Howrey Simon Arnold & White, LLP

(57) ABSTRACT

The present invention relates to methods of monitoring, via polymerase chain reaction, the clinical progression of human immunodeficiency virus infection and its response to antiretroviral therapy. According to the invention, polymerase chain reaction assays may be used to predict immunological decline and to identify, at an early stage, patients whose infection has become resistant to a particular antiretroviral drug regimen.

45 Claims, 10 Drawing Sheets-

OTHER PUBLICATIONS

Figure 1:
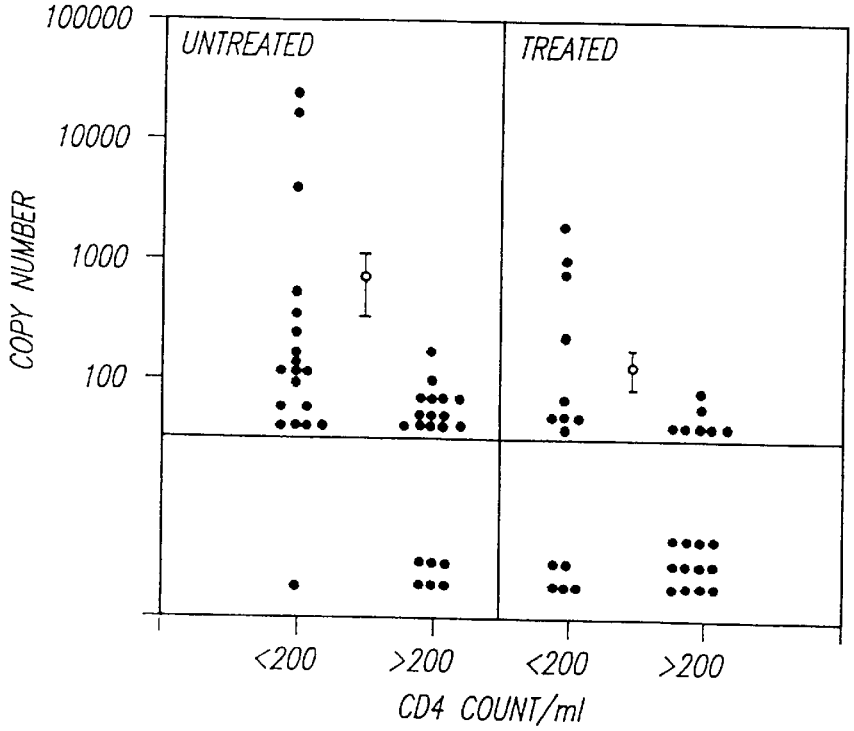

Henrard, et al., "A Sensitive Viral Capture Assay for Detection of Plasma veremia in HIV–Infected Individuals," *AIDS Res. Hum. Retrovirus,* 8:47–52.

Hewlett, et al., (1988) "Detection in Plasma of HIV–1 Specific DNA and RNA by Polymerase Chain Reaction Before and After Seroconversion," *J. Clin. Immunoassay,* 11:161–164.

Ho, et al., (1989) "Quantitation of Human Immunodeficiency Virus Type 1 in the Blood of Infected Persons," *N. Engl. J. Med.,* 321:1621–1625.

Holodniy, et al., (1991) "Inhibition of Human Immunodeficiency Virus Gene Aplification by Heparin," *J. Clin. Microbiol.,* 29:676–679.

Holodniy, et al., (1991) "Reduction in Plasma Human Immunodeficiency Virus Ribonucleic Acid after Dideoxynucleoside Therapy as Determined by the Polymerase Chain reaction," *J. Clin. Invest.,* 88:1755–1759.

Holodniy, et al., (1991) "Detection and Quantification of Human Immunodeficiency Virus RNA in Patient Serum by Use of the Polymerase Chain Reaction," *J. Infect. Dis.,* 163:862–866.

Japour, et al., (1991), "Detection of Human Immunodeficiency Virus Type 1 Clinical Isolates With Reduced Sensitivity to Zidovudine and Dideoxyinosine by RNA–RNA Hybridization," *Proc. Natl. Acad. Sci. USA,* 88:3092–3096.

Karpas, et al., (1990) "Polymerase Chain Reaction Evidence for Human Immunodeficiency Virus 1 Neutralization by Passive Immunization in Patients with AIDS and AIDS–related Complex," *Proc. Natl. Acad. Sci. USA,* 87:7613–7617.

Kawasaki, (1990) "In PCR Protocols: A guide to Methods and Applications," pp. 21–27, M. A. Innis, D. H. Gelfand, J. J. Sninsky, and T. J. White, eds. Academic Press, Berkeley, California.

Kellam, et al., (1992) "Fifth Mutation in Human Immunodeficiency Virus Type 1 Reverse Transcriptase Contributes to the Development of High–Level Resistance to Zidovudine," *Proc. Natl. Acad. Sci USA,* 89:1934–1938.

Kellog, et al., (1990) "In PCR Protocols: A Guide to Methods and Applications," pp. 337–347, M. A. Innis, D. H. Gelfand, J. J. Sninsky, and T. J. White, eds. Academic Press, Berkeley, California.

Kozal et al, (1993) "A mutation in Human Immunodeficiency Virus Reverse Transcriptase and Decline in CD4 Lymphociyte Numbers in Long–Term Zidovudine Recipients," *Journal of Infectious Diseases,* 167, 526–32.

Kusumi, et al., (1992) "Human Immunodeficiency Virus Type 1 Envelope Gene Structure and Diversity In Vivo and After Cocultivation In Vitro," *J. Virol. Methods,* 66:875–885.

Land, et al., (1990) "Decreased In Vitro Susceptibility to Zidovudine of HIV Isolates Obtained from Patients with AIDS," *J. Infect. Dis.,* 161:326–329.

Larder, et al., (1989) "HIV with Reduced Sensitivity to Zidovudine (AZT) Isolated During Prolonged Therapy," *Science,* 243:1731–1734.

Larder, et al., (1991) "Zidovudine Resistance Predicted by Direct Detection of Mutations in DNA From HIV–Infected Lymphocytes," *AIDS,* 5:137–144.

Larder, et al., (1989) "Multiple Mutations in HIV–1 Reverse Transcriptase Confer High–Level Resistance to Zidovudine (AZT)," *Science,* 246:1155–1158.

Levenson, et al., (1990) "In PCR Protocols: A Guide to Methods and Applications," pp. 99–112, M. A. Innis, D. H. Gelfand, J. J. Sninsky, and T. J. White, eds. Academic Press, Berkeley, California.

McElrath, et al., (1991) "Latent HIV–1 Infection in Enriched Populations of Blood Monocytes and T Cells from Seropositive Patients," *J. Clin. Invest.,* 87:27–30.

Meyerhans, et al., (1989) "Temporal Fluctations in HIV Quasispecies In Vivo Are Not Reflected by Sequential HIV Isolations," *Cell,* 58:901–910.

Murakawa, et al., (1988) "Direct Detection of HIV–1 RNA from AIDS and Arc Patient Samples," *DNA,* 7(4):287–295.

Ottman, et al., (1991) "The Polymerase Chain Reaction for the Detection of HIV–1 Genomic RNA in Plasma From Infected Individuals," *J. Virol. Methods,* 31:273–184.

Richman, et al., (1991) "Detection of Mutations Associated with Zidovudine Resistance in Human Immunodeficiency Virus by Use of the Polymerase Chain Reaction," *J. Infect. Dis.,* 164:1075–1081.

Richman, et al., (1990) "Effect of Stage of Disease and Drug Dose on Zidovudine Susceptibilities of Isolates of Human Immunodeficiency Virus," *J. Aids,* 3:743–746.

Rooke, et al., "Isolation of Drug–Resistant Variants of HIV–1 From Patients on Long–Term Zidovudine Therapy," *AIDS,* 3:411–415.

Semple, et al., (1991) "Direct Measurement of Viraemia in Patients Infected With HIV–1 and Its Relationshjip to Disease Progression and Zidovudine Therapy," *J. Virol. Methods,* 35:38–45.

Shafer RW, et al., "Combination therapy with zidovudine and didanosine selects for drug–resistant human deficiency virus type 1 strains with unique patterns of pol gene mutations," *J. Infect. Dis.,* 169:722–9.

Shirasaka T., et al., "Changes in drug sensitivity of human immunodeficiency virus type 1 during therapy with azidothymidine, dideoxycytidine, and dideoxyinosine; an in vitro comparative study," *Proc. Natl. Acad. Sci. USA,* 90:562–6.

St. Clair, MH, et al., "Resistance to ddl and sensitivity to AZT induced by a mutation in HIV–1 reverse transcriptase," *Science,* 253:1557–9.

Stragene catalog, (1988), p. 39.

Tersmette, et al., (1989) "Association Between Biological Properties of Human Immunodeficiency Virus Variants and Risk for AIDS and AIDS Mortality," *Lancet,* 1:983–985.

Tudor–Williams, et al., (1992) "HIV–1 Sensitivity to Zidovudine and Clinical Outcome in Children," *Lancet,* 339:15–19.

Volberding, et al., (1990) "Zidovudine in Asymptomatic Human Immunodeficiency Virus Infection," *N. Engl. J. Med.,* 322:941–949.

Yerly, et al., (1992) Quantitation of Human Immunodeficiency Virus Provirus and Circulating Virus: Relationship with Immunologic Parameters, *J. Infect. Dis.,* 166:269–76.

Aoki, et al., (1990) "Quantitative Analysis of HIV–1 Proviral DNA in Peripheral Blood Mononuclear Cells from Patients with AIDS or ARC: Decrease of Provital DNA Content Following Treatment with 2',3'–Dideoxyinosine (DDL)," *AIDS Res. Hum. Retroviruses,* 6:1331–1339.

Bagnarelli, et al., (1991) "Detection of Human Immunodeficiency Virus Type 1 Genomic RNA in Plasma Samples by Reverse–Transcription Polymerase Chain Reaction," *J. Med. Virol.,* 34:89–95.

Boucher, et al., (1990) "Zidovudine Sensitivity of Human Immunodeficiency Viruses from High–Risk Symptom–Free Individuals During Therapy," *Lancet,* 336:585–590.

FIG. 6

| PBMC \ SERUM | WILDTYPE | MUTANT |
|---|---|---|
| WILDTYPE | 11 | 10 |
| MUTANT | 0 | 17 |

FIG. 7

HIV 1
gag (p24) CORE PROTEIN

| NAME | OLIGO 1 |
|---|---|
| SK 38 | 5′-ATA ATC CAC CTA TCC CAG TAG GAG AAAT (SEQ ID NO: 1) |
| | OLIGO 2 |
| SK 39 | 5′-TTT GGT CCT TGT CTT ATG TCC AGA ATG C (SEQ ID NO: 2) |
| | PROBE |
| SK 19 | 5′- ATC CTG GGA TTA AAT AAA ATA GTA AGA ATG TAT AGC CCT AC (SEQ ID NO: 3) |

FIG. 8

74 WT: 5′-AAGTTCTCTGAAATCTACTTA-3′ (SEQ ID NO:5)
74MUT: 5′-AAGTTCTCTGAAATCTACTTC-3′ (SEQ ID NO:6)
X2: 5′-AACAATGGCCATTGACAGA-3′ (SEQ ID NO: 4)

POLYMERASE CHAIN REACTION ASSAYS FOR MONITORING ANTIVIRAL THERAPY AND MAKING THERAPEUTIC DECISIONS IN THE TREATMENT OF ACQUIRED IMMUNODEFICIENCY SYNDROME

Matter enclosed in heavy brackets [ ] appears in the original patent but forms no part of this reissue specification; matter printed in italics indicates the additions made by reissue.

This application is a continuation application of U.S. application Ser. No. 08/290,311, filed Aug. 15, 1994, now U.S. Pat. No. 5,631,128, which is a continuation-in-part application of U.S. application Ser. No. 07/883,327, filed May 14, 1992, abandoned.

This invention was made with Government support under contracts AI27762-04 and AI27766-07 awarded by the National Institutes of Health. The Government has certain rights in this invention.

1. INTRODUCTION

The present invention relates to methods of monitoring, via polymerase chain reaction, the clinical progression of human immunodeficiency virus infection and its response to antiretroviral therapy. According to the invention, polymerase chain reaction assays may be used to predict immunological decline and to identify, at an early stage, patients whose infection has become resistant to a particular antiretroviral drug regimen.

2. BACKGROUND OF THE INVENTION

Human immunodeficiency virus (HIV) isolated from patients treated with zidovudine (AZT) may demonstrate markedly reduced in vitro susceptibility to AZT (Larder et al., 1989, Science 243:1731–1734; Rooke et al., 1989, AIDS 3:411–415; Land et al., 1990, J. Infect. Dis. 161:326–329; Boucher et al., 1990, Lancet 336:585–590; Japour et al., 1991, Proc. Natl. Acad. Sci. 88:3092–96; Tudor-Williams et al., 1992, Lancet 339:15–19). This reduced susceptibility has been related to the duration of therapy with AZT and the severity of HIV disease at the time AZT therapy is begun (Richman et al., 1990, AIDS 3:743–756). Nucleotide sequence analysis of AZT-resistant HIV strains has revealed a number of mutations in the reverse transcriptase (RT) gene associated with decreased AZT susceptibility (Larder et al., 1989, Science 246:1155–1158; Larder et al., 1991, AIDS 5:4137–144; Kellam et al., 1992, Proc. Natl. Acad. Sci. USA 89:1934–1938; St. Clair et al., 1991, Science 253:1557–1559; Richman et al., 1991, J. Infect. Dis. 164:1075–1081). Molecular cloning experiments have confirmed that these mutations in the RT gene confer AZT resistance (Larder et al., 1989, Science 246:1155–1158; Larder et al., 1991, AIDS 5:137–144; Kellam et al., 1992, Proc. Natl. Acad. Sci. USA 89:1934–1938; St. Clair et al., 1991, Science 253:1557–1559). Of these mutations the one at codon 215 resulting in a single amino acid substitution (Thr→Tyr or Phe) has been shown to be the most common mutation and to have the greatest impact on in vitro susceptibility to AZT (Larder et al., 1991, AIDS 5:137–144; Richman et al., 1991, J. Infect. Dis. 164:1075–1081; Boucher et al., 1992, J. Infect. Dis. 165:105–110).

Several studies have addressed the relationship between in vitro AZT resistance, mutations in the RT gene and clinical disease. Richman and coworkers studied 32 patients with different stages of HIV disease and demonstrated that the development of in vitro AZT resistance was related to the duration of therapy with AZT and to the severity of disease at the time AZT was begun (Richman et al., 1990, AIDS 3:743–746). Boucher and coworkers studied HIV P24-antigenemic patients treated with AZT for 2 years. They observed that at 6 months, seven patients with a mutation at codon 215 had a weak, non-statistically significant trend toward lower CD4 counts compared to nine patients who were wild type at codon 215 (Boucher et al., 1990, Lancet 336:585–590). After 2 years nearly all patients had the mutation. Tudor-Williams and coworkers studied HIV isolates from 19 symptomatic children treated with AZT for 9–39 months and showed that in vitro AZT resistance was associated with poor clinical outcome (Tudor-Williams et al., 1992, Lancet 339:15–19).

Kahn and colleagues (Kahn et al., 1992, N. Engl. J. Med. 327:581–587) reported that patients infected with HIV who have relatively advanced disease and at least 16 weeks of previous zidovudine therapy may have clinical benefit if switched to didanosine monotherapy instead of remaining on zidovudine. The reason patients benefit from switching from zidovudine to didanosine is not fully understood, but one possibility is that dididanosine is suppressing zidovudine-resistant HIV.

Increasing evidence exists of a correlation between zidovudine-resistant HIV and disease progression in patients treated with zidovudine monotherapy (Tudor-Williams et al., 1992, Lancet 339:15–19; St. Clair et al., 1993, AIDS 6:891–897; Kozal et al., 1993, J. Infect. Dis. 167:526–532; Montaner et al., 1993, AIDS 7:189–196). It has been shown that HIV can also develop resistance to didanosine (ddI)(St. Clair et al., 1991, Science 253:1557–1559; Reichman et al., 1993, Antiviral Res. 20:267–277; Japour et al., 1991, Proc. Natl. Acad. Sci. USA 88:3092–3096). As with the resistance of HIV to zidovudine, the decrease in susceptibility of HIV to didanosine has been shown to be caused by specific mutations in the HIV reverse-transcriptase gene. St. Clair and colleagues (St. Clair et al., 1991, Science 253:1557–1559) identified the first mutation in the reverse-transcriptase gene to confer resistance to didanosine, a mutation at codon 74 that results in an amino acid change from leucine to valine. The codon 74 mutation in an HIV construct can induce an eightfold decrease in susceptibility to didanosine.

Although other mutations have been reported to confer didanosine resistance (Gu et al., 1992, J. Virol. 66:28–35), most data to date suggest the codon 74 mutation is the primary mutation responsible for didanosine resistance in patients receiving didanosine monotherapy.

3. SUMMARY OF THE INVENTION

The present invention relates to methods of monitoring, via polymerase chain reaction (PCR), the clinical progression of human immunodeficiency virus (HIV) infection and its response to antiviral therapy. It is based, in part, on the discovery that plasma HIV RNA copy number, as measured using PCR, may be used as a sensitive marker of the circulating HIV viral load to assess the therapeutic effect of antiretroviral compounds. In working examples described herein, an increase in plasma HIV RNA copy number was found to correlate with disease progression, and successful antiretroviral therapy was found to correlate with a decline in plasma HIV RNA copy number.

The invention is also based, in part, on the discovery that genetic changes in HIV which confer resistance to antiretroviral therapy may be rapidly determined directly from patient peripheral blood mononuclear cells (PBMC) and/or plasma HIV RNA using a "nested" PCR procedure. In working examples disclosed herein, a mutation at codon 215 of HIV reverse transcriptase (RT) was found to occur in AZT-treated patients which correlated with refractoriness to AZT treatment. The mutation was found in plasma HIV RNA one to eight months before it was detectable in PBMC. The development of the codon 215 mutation in HIV RT was found to be a harbinger of immunological decline, which occurred between six and twelve months after the mutation was detectable in plasma HIV RNA.

In particular embodiments of the invention, PCR assay may be used to monitor the clinical progression of HIV infection in patients receiving antiretroviral therapy. An increase in plasma HIV copy number detected by such an assay would correlate with refractoriness to treatment. If a patient being treated with an antiretroviral therapeutic agent exhibits an increase in plasma HIV RNA copy number, a physician should consider altering the patients treatment regimen. It should be noted that the present invention offers the advantage of being more sensitive in measuring HIV virus than standard methods which measure plasma p24 antigen or infectious virus detectable by culture techniques.

In further embodiments of the invention, PCR assay may be used to detect mutations at codon 215 of HIV RT which correlate with resistance to antiretroviral therapy and which precede immunologic decline by 6–12 months. Once mutation at codon 215 has been detected in a patient undergoing antiretroviral therapy, an alteration in the therapeutic regimen must be considered. The speed at which a modified regimen should be instituted may depend on whether the mutation is present in plasma HIV RNA or PBMC. If the mutation is present in PBMC, a rapid alteration in therapy may be warranted.

In further embodiments of the invention, PCR assay may be used to detect and monitor the absolute concentrations and relative proportions of virus which mutations at codon 74 of HIV RT, a mutation which correlates with resistance to therapy with didanosine (ddI). When mutation at codon 74 has been detected in patient undergoing monotherapy with ddI, an alteration in the therapeutic regimen must be considered. Such alteration may include combination therapy, e.g. ddI and AZT, or combination therapy with another antiviral agent.

In patients suffering from HIV infection, opportunistic infections arising as a result of a compromised immune system can be rapidly fatal. It is therefore extremely important to strive to avoid deterioration of the immune system in these patients. Because the present invention enables the early prediction of immunological decline, it allows alteration of a patient's therapeutic regimen so as to avoid opportunistic infections, and therefore may be used to promote survival and improve the quality of life of HIV-infected patients.

4. DESCRIPTION OF THE FIGURES

FIG. 1. Human immunodeficiency virus RNA copy number in 200 $\mu$l of plasma from 72 subjects as determined by cDNA gene amplification. Of 39 patients who were not currently receiving antiretroviral therapy, 20 had a CD4 count <200/mm$^3$ (HIF copy number 1.369±707) and 19 had a CD4 count >200/mm$^3$ (HIV copy number 44±10). Of 33 subjects who were currently on AZT, 14 had a CD4 count <200/mm$^3$ (HIV copy number 295±5) and 19 had a CD4 count >200/mm$^3$ (HIV copy number 16±5). Mean copy number (open circles) of subjects not on therapy was 690±360 as compared to 134±219 for patients currently on AZT (P<0.05, independent sample t test).

Figure 2:
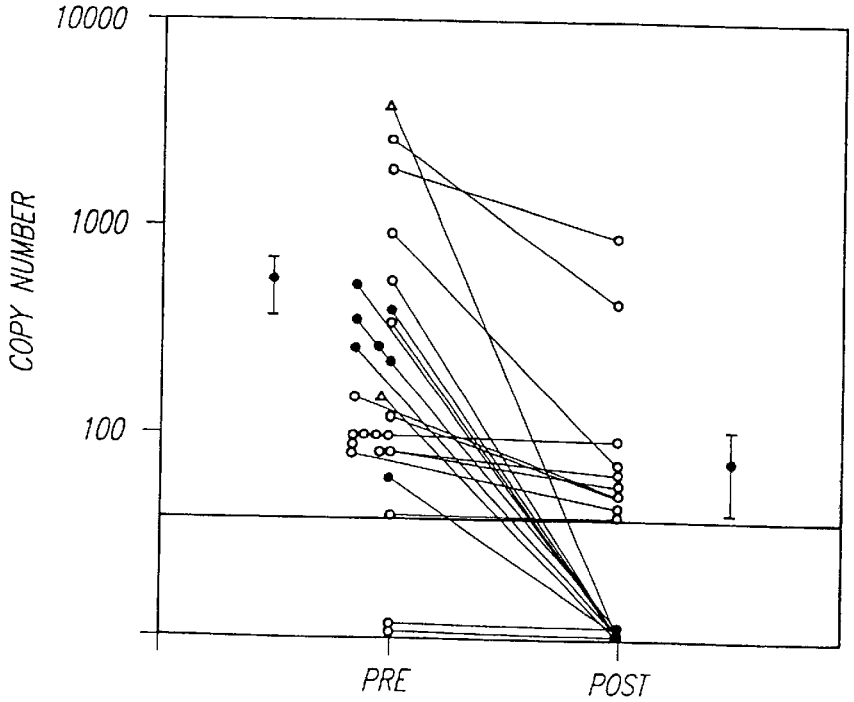

FIG. 2. Human immunodeficiency virus RNA copy number in plasma from 27 subjects before (pre) and 1 mo after (post) dideoxynucleoside therapy. (o) AZT; (●) AZT+ddI; and (▲) ddI alone. Mean copy number decreased from 540±175 to 77±35 after therapy (P<0.05 paired t test).

Figure 3:
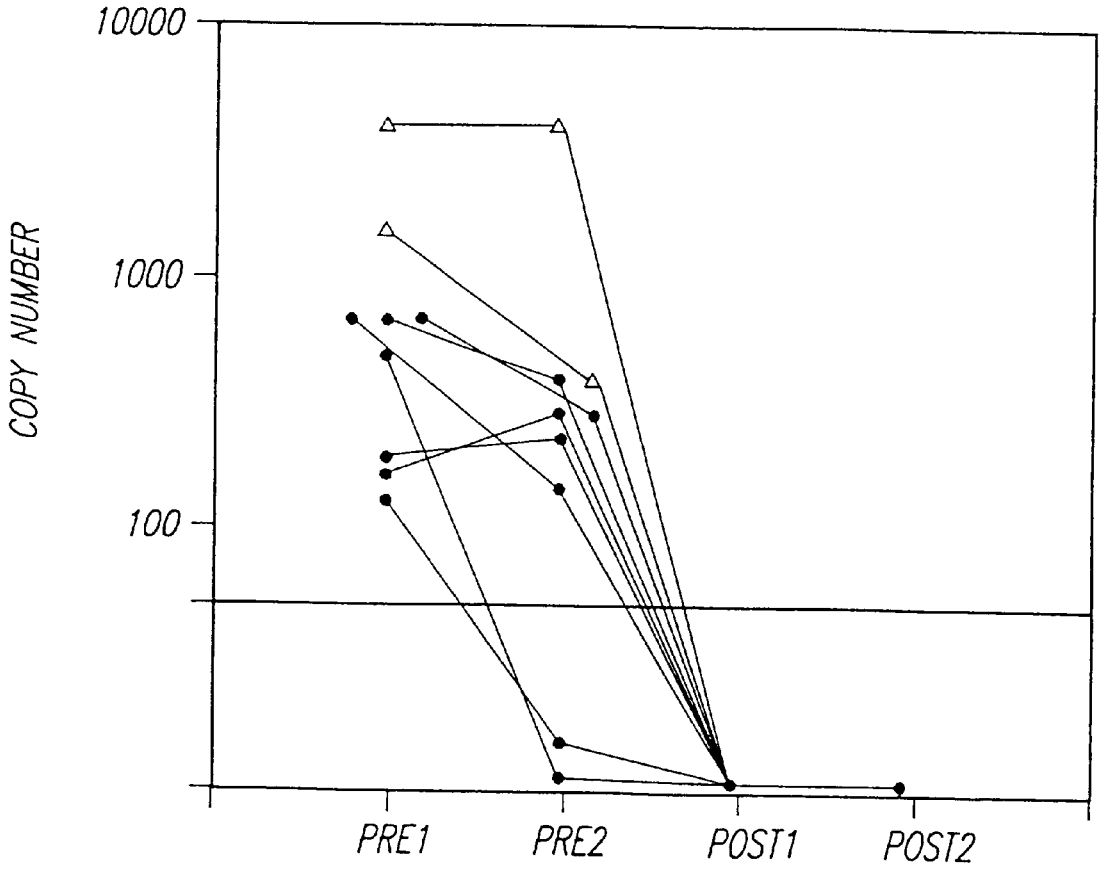

FIG. 3. Human immunodeficiency virus RNA copy number in plasma from 9 subjects with two samples obtained before initiation of therapy (pre 1 and pre 2) and two samples obtained 1 and 2 mo after commencing therapy (post 1 and post 2). (▲) ddI alone; (●) ddI+AZT.

Figure 4A:
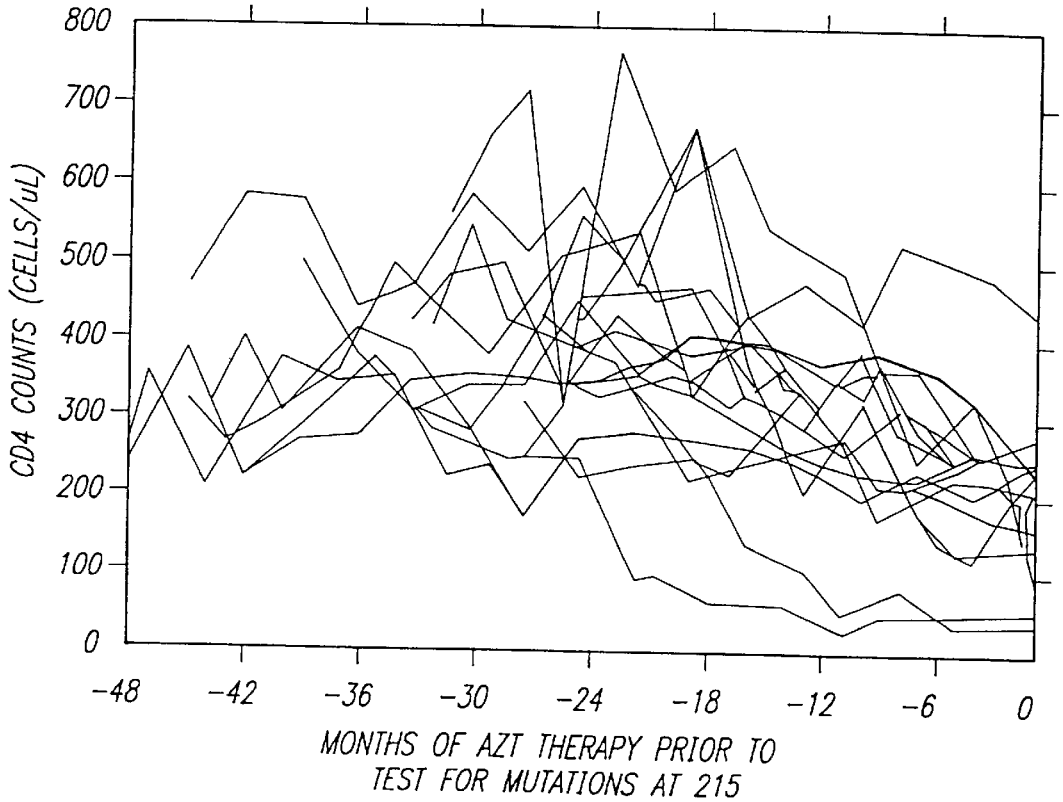
Figure 4B:
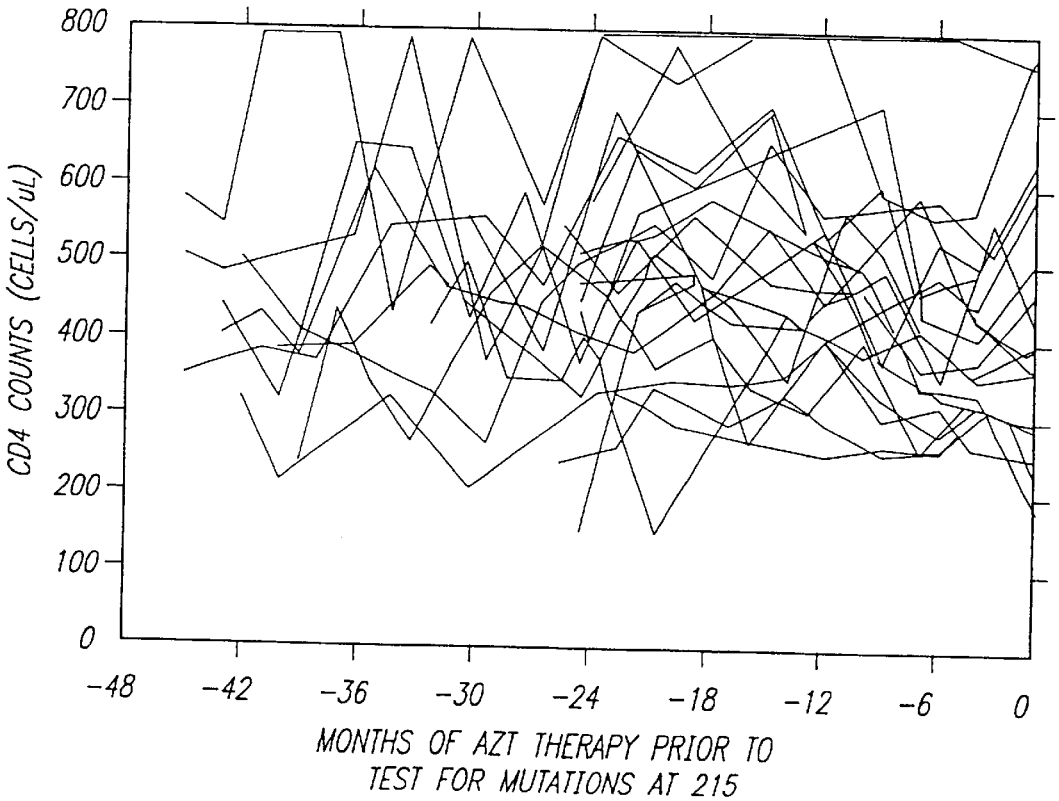

FIGS. 4A and 4B. Serial CD4 counts in PBMC (cells/$\mu$l) of 17 patients in which HIV reverse transcriptase carried a mutation at codon 215 (FIG. 4A) and of 21 patients in which HIV reverse transcriptase was wild type at codon 215 (FIG. 4B).

Figures 1, 5A:
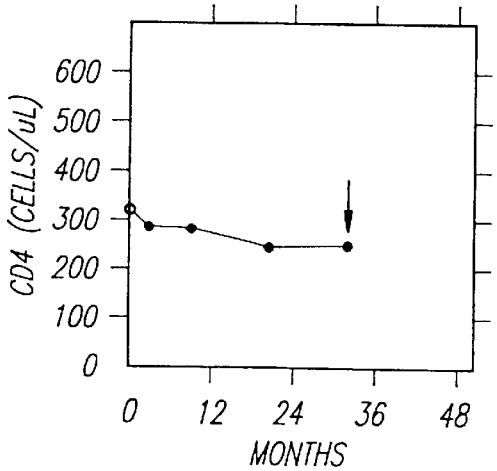
Figures 2, 5A:
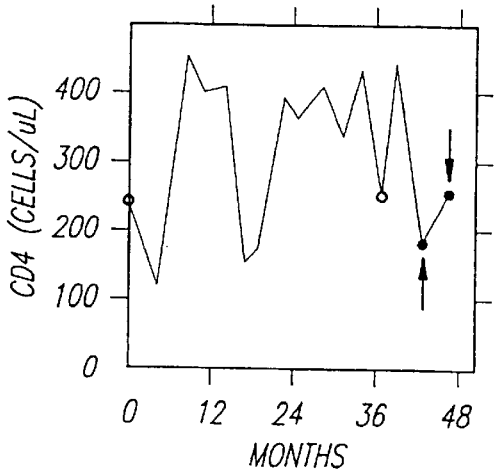
Figures 3, 5A:
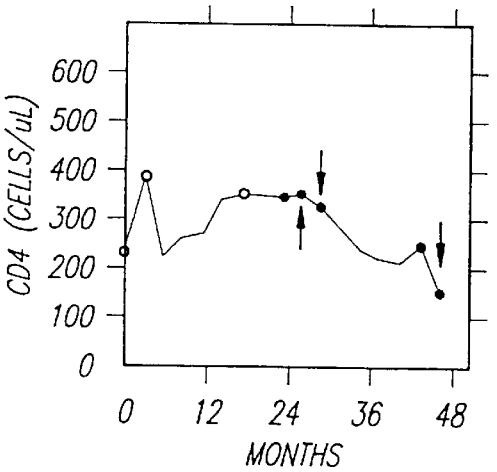
Figures 4, 5A:
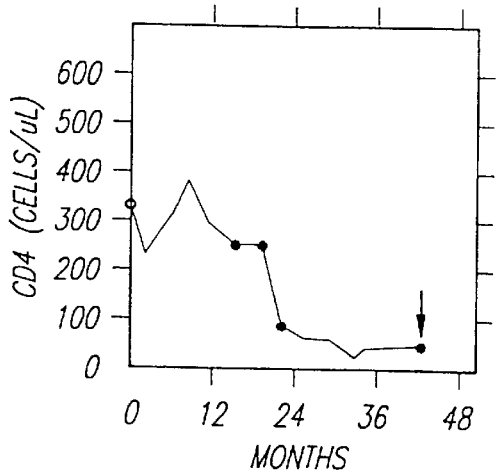
Figures 5, 5A:
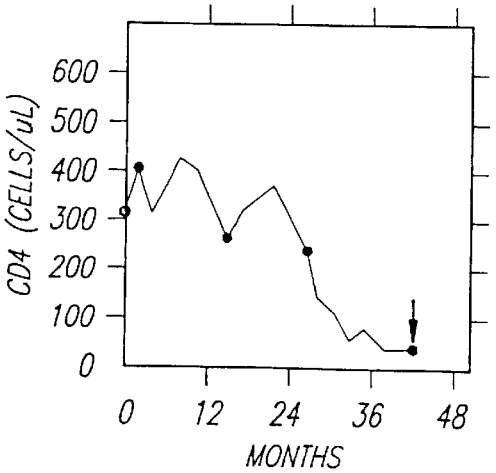
Figures 5, 5A, 6:
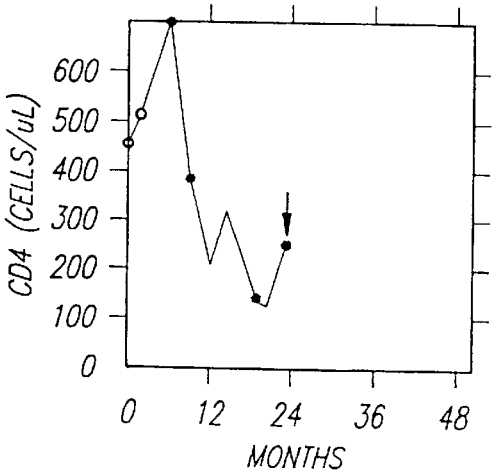
Figures 5, 5A, 6, 7:
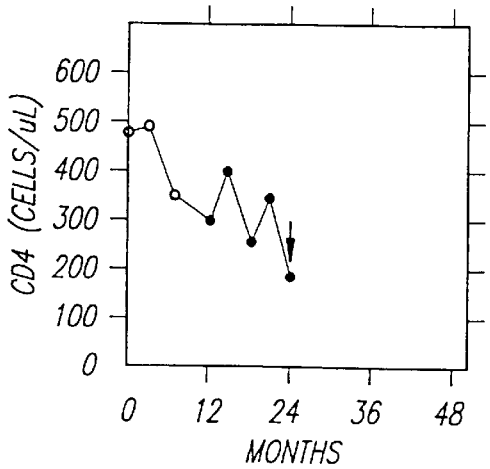
Figures 5, 5A, 6, 7, 8:
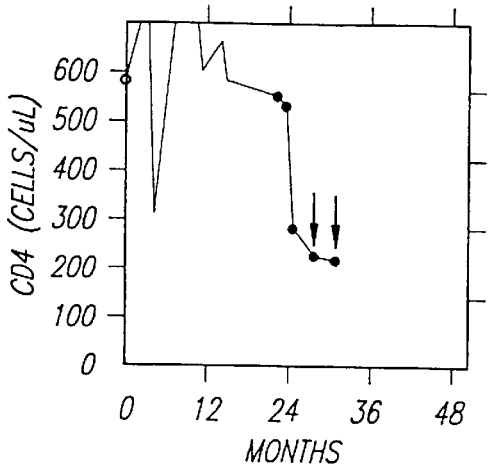
Figures 5, 5A, 6, 7, 8, 9:
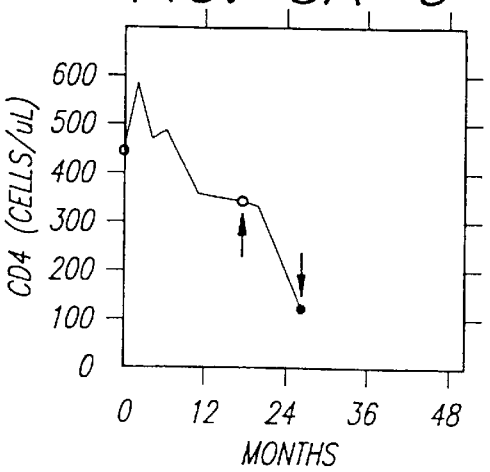
Figures 5, 5A, 6, 7, 8, 9, 10:
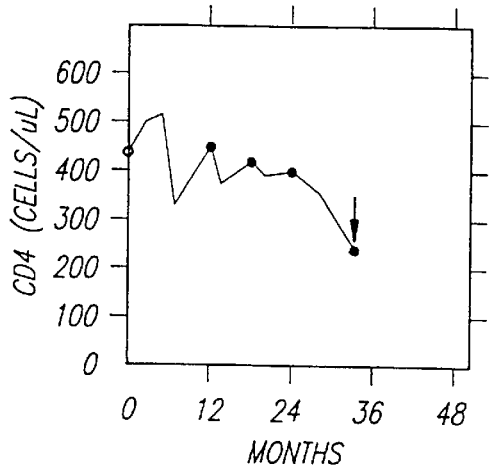
Figures 5, 5A, 6, 7, 8, 9, 10, 11:
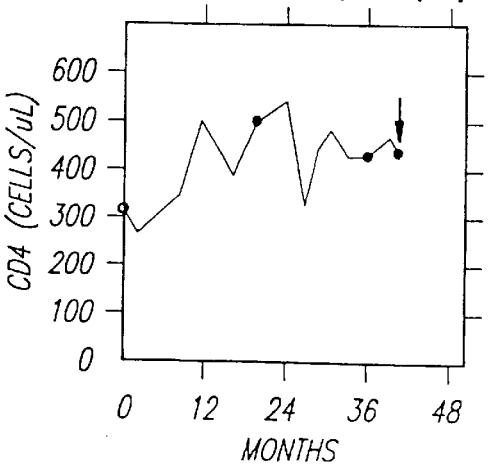
Figures 5, 5A, 6, 7, 8, 9, 10, 11, 12:
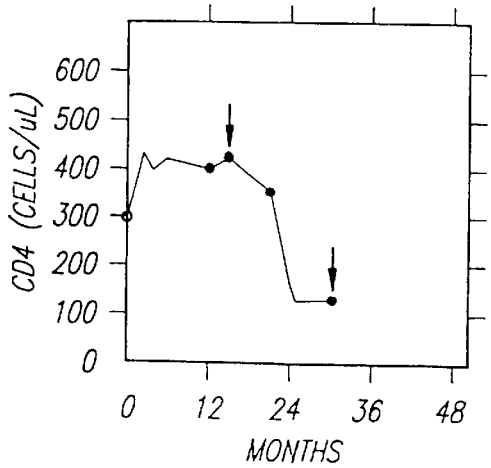
Figures 5, 5A, 6, 7, 8, 9, 10, 11, 12, 13:
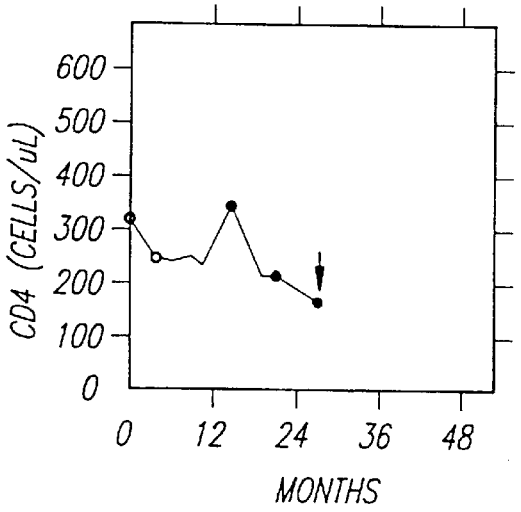
Figures 5, 5A, 6, 7, 8, 9, 10, 11, 12, 13, 14:
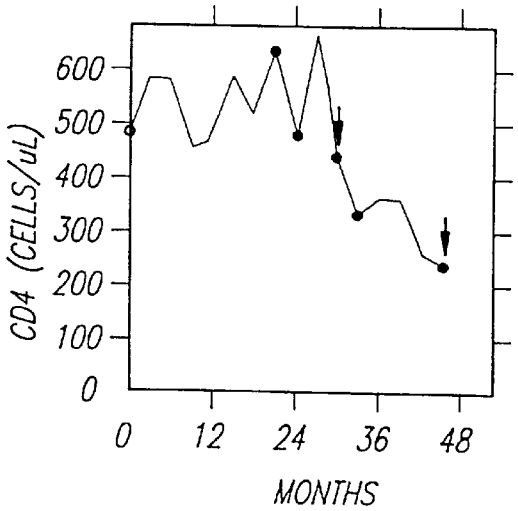
Figures 5, 5A, 6, 7, 8, 9, 10, 11, 12, 13, 14, 15:
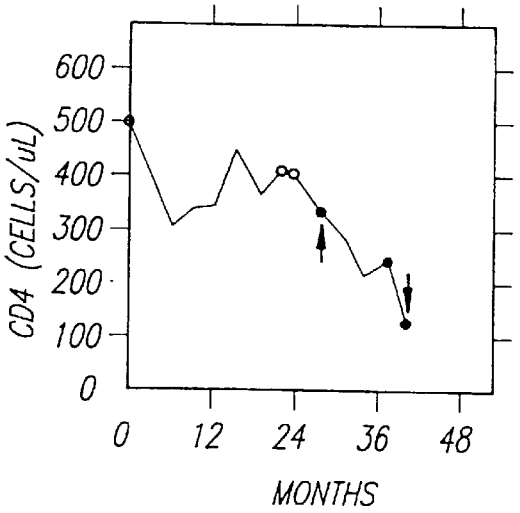
Figures 5, 5A, 6, 7, 8, 9, 10, 11, 12, 13, 14, 15, 16:
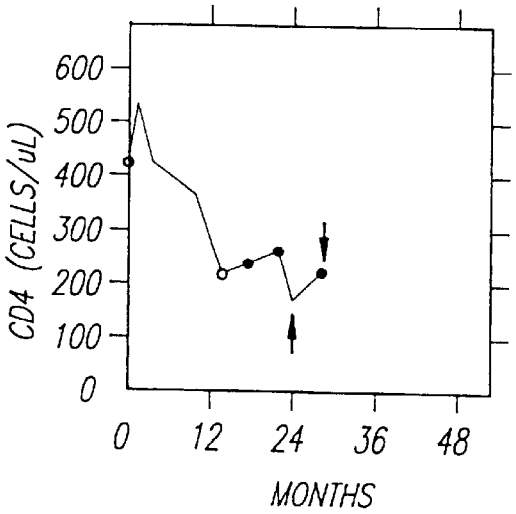
Figures 1, 5B:
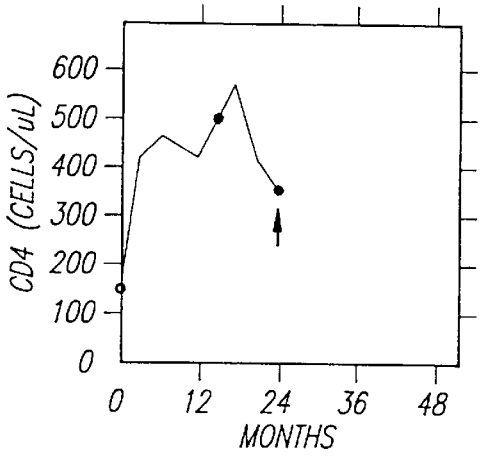
Figures 2, 5B:
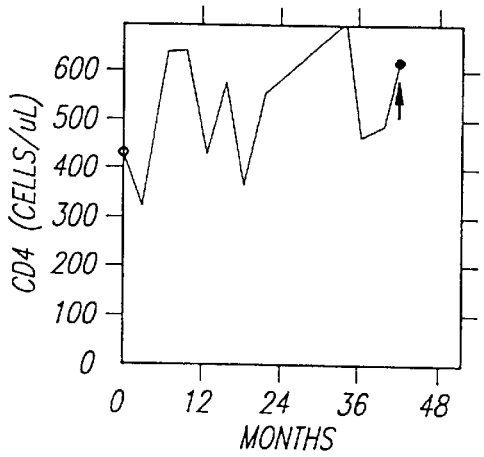
Figures 3, 5B:
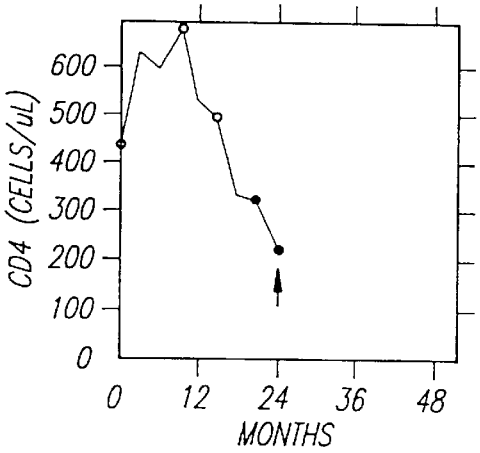
Figures 4, 5B:
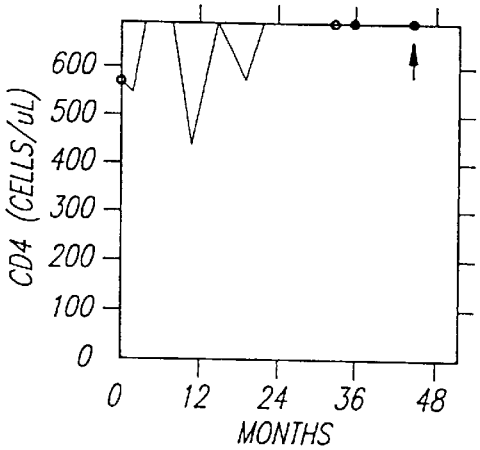
Figures 5, 5B:
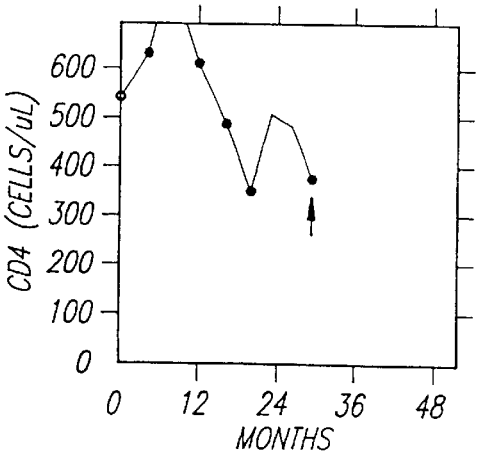
Figures 5, 5B, 6:
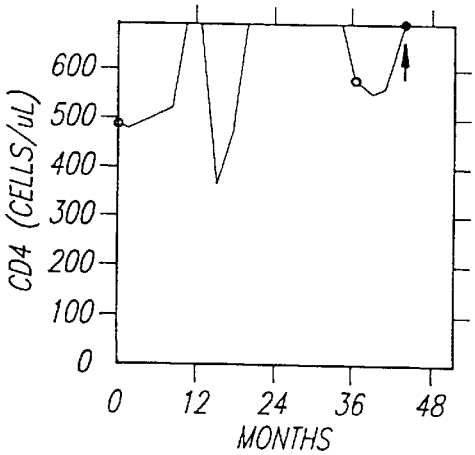
Figures 5, 5B, 6, 7:
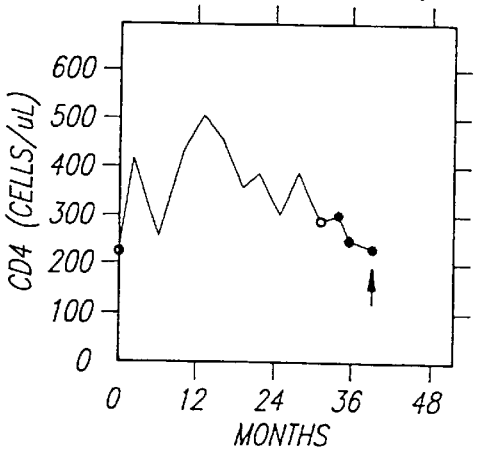
Figures 5, 5B, 6, 7, 8:
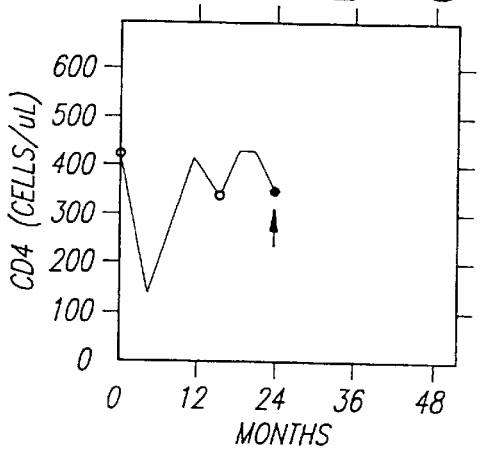
Figures 5, 5B, 6, 7, 8, 9:
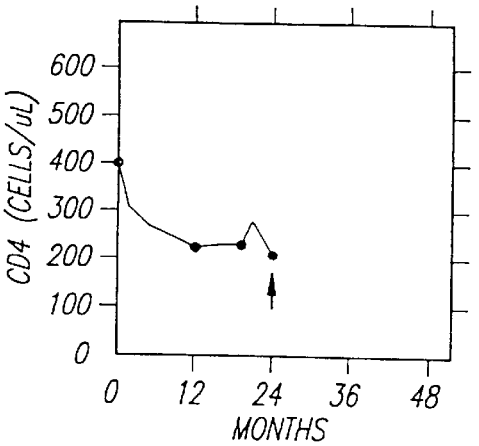
Figures 5, 5B, 6, 7, 8, 9, 10:
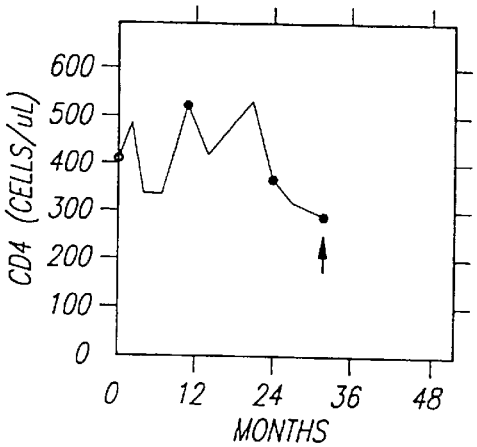
Figure 5C:
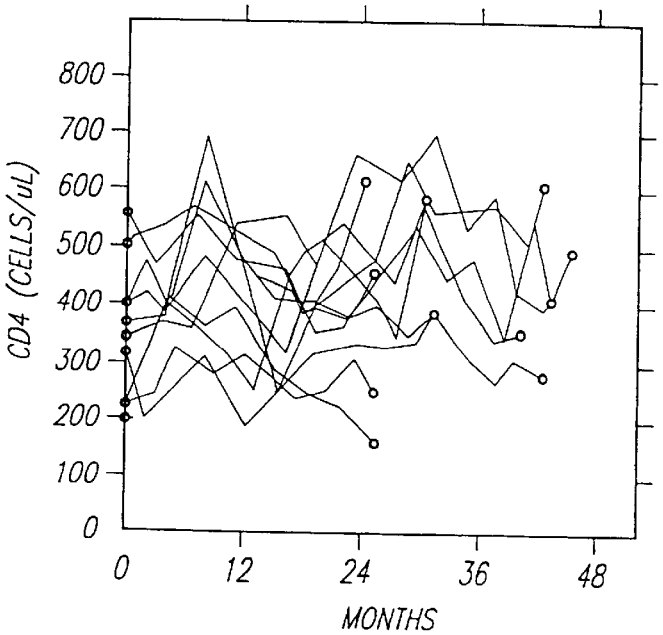
Figure 9:
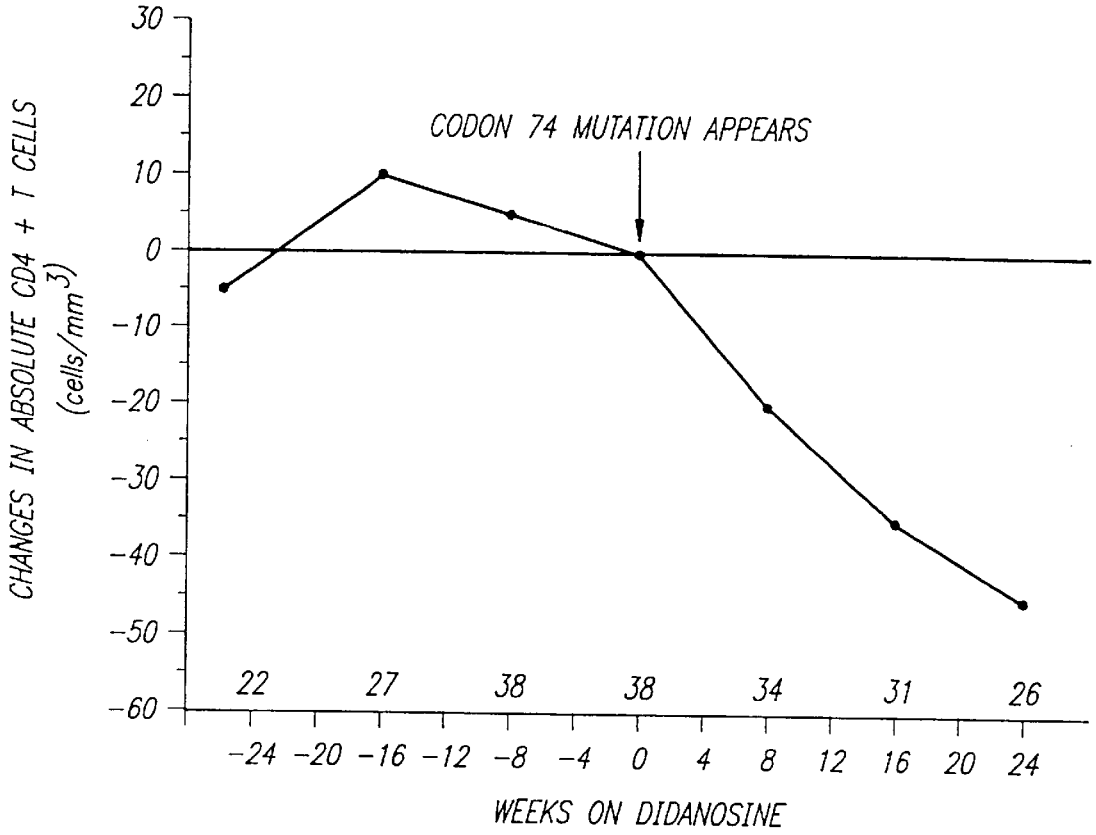

FIGS. 5A1 to 5A16, 5B1 to 5B10, and 5C. CD4 cell counts in PBMC from serial time points in 37 patients. o=wild type sequence in serum specimen. ●=mutant sequence in serum. ↑=wild type sequence in PBMC, ↓=mutant sequence in PBMC; FIG. 5A: 16 patients mutant at codon 215 in both serum HIV RNA and PBMC (proviral DNA). FIG. 5B: 10 patients mutant at codon 215 in serum HIV RNA but wild type in their PBMC. FIG. 5C: 11 patients whom remained wild type at codon 215 in their serum HIV RNA and PBMC.

FIG. 6. Relationship of PBMC to serum genotypes in the 38 patients at study endpoint.

FIG. 7. Nucleotide sequences of SK38(SEQ ID NO:1), SK39(SEQ ID NO:2), and SK19(SEQ ID NO:3).

FIG. 8. Nucleotide sequences of primers X2(SEQ ID NO:4), 74WT(SEQ ID NO:5), and 74MUT(SEQ ID NO:6).

FIG. 9. Mean CD4$^+$ T-cell changes before the appearance of the HIV reverse-transcriptase mutation at codon 74 and changes in the CD4$^+$ T cells after the appearance of the mutation in 38 patients switched from zidovudine to didanosine. The point of the codon 74 mutation (measured in the serum HIV RNA of the patients) is at time 0 and is the reference point for all other CD4$^+$ T-cell counts to be compared; x-axis, −24 to 0 represents the time receiving didanosine before the codon 74 mutation and 0 to 24 represents the time receiving didanosine after the mutation. The y-axis represents the mean CD4$^+$ T-cell change in relation to the CD4$^+$ T-cell level at the time of the mutation. The number of patients evaluable are above each time point.

5. DETAILED DESCRIPTION OF THE INVENTION

The present invention relates to methods of monitoring, via PCR, the clinical progression of HIV infection in patients receiving antiretroviral therapy. For purposes of clarity and not by way of limitation, the detailed description of the invention is divided into the following subsections:

(i) PCR assay of plasma HIV RNA;

(ii) PCR assay of peripheral blood mononuclear cells;

(iii) PCR assay for mutation at codon 215 of HIV reverse transcriptase;

(iv) PCR assay for mutation at codon 74 of HIV reverse transcriptase; and (v) utility of the invention.

It should be noted that heparin appears to have an inhibitory effect on gene amplification via PCR. It is therefore desirable to avoid using heparin as an anticoagulant of patient blood samples. If heparin has been used in a sample, the sample may be purified of heparin, for example, by collecting virus by ultracentrifugation.

5.1 PCR ASSAY OF PLASMA HIV RNA

According to the invention, it is desirable to avoid degradation of RNA in plasma samples prior to measurement of HIV RNA copy number. Therefore, in preferred embodiments of the invention, guanidinium is added to plasma or serum samples prior to storage at a concentration of about 2.5M and samples are kept frozen at −70° C., with no samples stored for longer than about 3 months. Serum may be used interchangeably with plasma according to the invention.

RNA may be extracted from plasma using standard techniques, such as those set forth in Chomczynski and Sacchi, 1987, Ann. Biochem. 162:156–159. For example, 200 μl of clarified plasma to which 200 μl of 5M guanidinium thiocyanate had previously been added may be extracted with phenol/chloroform and precipitated with isopropanol. The resulting pellet may then be washed in 75 percent ethanol, dried, and brought up into solution in diethylpyrocarbonate-treated glass distilled water.

From plasma RNA, HIV RNA may be transcribed to cDNA using a suitable reverse transcriptase (for example, Moloney murine leukemia virus reverse transcriptase) using standard techniques, such as for example, those set forth in Kawasaki, 1990, in "PCR Protocols: A Guide to Methods and Applications," Innis et al., eds. Academic Press, Berkeley, Calif. pp. 21–27. Any suitable primer for amplification of HIV genomic RNA sequences may be used, include, but not limited to, the oligomers SK38, SK39, and SK19 (FIG. 7) described in Kellog et al., 1990, in "PCR Protocols: A Guide To Methods and Applications," Innis et al., eds., Academic Press, Berkeley, Calif. pp. 337–347. In a preferred embodiment of the invention, HIV cDNA may be amplified as follows: to a 100 μl reaction mixture, cDNA prepared as described supra may be added, together with 50 pmol of primers SK38 and SK39, 10 mM of each dNTP, 10 mM Tris (pH 8.3), 2.5 mM $MgCl_2$, 50 mM KCl, and 2.5 U of recombiTaq DNA polymerase (Perkin-Elmer Cetus, Norwalk, Conn.). The mixture may then be overlaid with 50 gl of mineral oil, and tubes containing the reaction may be placed in a DNA thermal cycler (e.g. Perkin-Elmer Cetus) for about 30 cycles of amplification with the following program: 95° C./30 seconds, 55° C./30 seconds, and 72° C./60 seconds for denaturation, annealing, and extension, respectively. Negative and positive controls which include both high and low copy number HIV RNA and DNA may be added at each step.

The number of PCR cycles may be adjusted to amplify the DNA segments to detectable levels while retaining linearity. Usually the number of PCR cycles will be less than 40, often less than 35, and typically only about 30. If the amplified DNA is not readily detectable at 30 cycles, the PCR may be continued for a few cycles more, e.g. to 33 or 35, and reprobed.

The copy number of HIV RNA may then be measured by methods known to the skilled artisan. For example, the number of copies of HIV RNA in a patient sample may be quantiated by hybridizing the product of the above PCR with a detectably labeled probe that is complementary to HIV sequence. The amount of signal generated by probe hybridized to PCR product may then be compared to the amount of signal generated by probe hybridized to a known copy number of HIV. Probe may be detectably labeled by an enzyme, a radioisotope, a fluorescent compound, a chromogenic compound, or any other detectably labeled compound.

In a preferred, nonlimiting embodiment of the invention, at least one of the PCR primers may be biotinylated, probe may be labeled with horseradish peroxidase (HRP), and copy number may be evaluated by an enzyme-linked affinity assay as follows. 96-well microplates (Maxisorp; Nunc, Naperville, Ill.) may be coated with 100 μl of a 0.1 mg/ml solution of avidin (Sigma Chemical Co., St. Louis, Mo.) in 50 mM $Na_2CO_3$ (pH 9.6) overnight at room temperature. Wells may then be washed twice with PBS, and then filled with 300 μl of a blocking solution containing 5X Denhardt's solution, 1% gelatin (Sigma), 250 μl/ml sheared herring sperm DNA (Promega Biotec, Madison, Wis.) at least overnight at 4° C. Immediately before use, the blocking solution may be aspirated from each well and 5 μl of PCR product prepared as described supra (using at least one biotinylated primer) may be added to each well together with 65 μl of a hybridization solution containing 5× saline sodium phosphate EDTA, 5× Denhardt's solution; and 1 pmol of HRP-labeled SK19 HIV gag-specific probe. Because HIV primer was biotinylated, HIV amplified sequences should selectively adhere to the avidin-coated wells, so that a capture and hybridization reaction may be carried out for 1 hour at 42° C. Each well may then be washed about 20 times with PBS containing 0.05% Tween-20, for example, using a Biomek™ 1000 Automated Workstation (Beckman Instruments, Inc., Palo Alto, Calif.). The HRP substrate O-phenylenediamine (Sigma) may then be prepared at 0.6 mg/ml in 0.1M citrate buffer (pH 5.5) containing 0.03% hydrogen peroxide, and 150 μl of this solution may be added to each well. After about 10 minutes the reaction may be stopped with 1N $H_2SO_4$ and the optical density of each well measured at 490 nm, for example by the Biomek 1000. A lower level of positivity had been defined as an absorbance of 0.135. This cutoff value was calculated from the mean absorbance obtained from a group of seronegative samples plus three standard deviations. Copy number from subject samples may be determined from the absorbances obtained from a dilution series of an RNA gag gene construct of known copy number (Holodniy et al., 1991, J. Infect. Dis. 163:862–866).

In an alternate preferred, specific embodiment for detection of codon 215 mutations, RNA collected from plasma may be reverse-transcribed by using 500 ng of primer NEI (5'-TCATTGACAGTCCAGCT-3')(SEQ ID NO:7) and 200 units of MuLV RT (Bethesda Research Labs) in 10 μl of amplification buffer (25 mM kCL, 50 mM Tris HCl pH 8.3, 0.1 mg/ml bovine serum albumin, 1.45 mM each of dATP, dGTP, dCTP and dTTP, 1.5 mM $MgCl_2$, and 2.5 U of RNasin (Promega)) for 10 min. at room temperature, then 30 minutes at 42° C. followed by heat inactivation at 95° C. for 5 min. This cDNA may then be amplified by PCR using 250 ng of primer A (5'-TTCCCATTAGTCCTATT-3')(SEQ ID NO: 8) in a reaction mixture (100 μl) containing the same buffer as above with 0.25 mM of each dNTP and 2.5 U of Amplitaq DNA polymerase, using about 30 cycles of 94° C. for 1 min., 45° C. for 1 min, and 72° C. for 2 min, to generate a 768 bp region of the HIV pol gene.

5.2 PCR ASSAY OF PERIPHERAL BLOOD MONOMUCLEAR CELLS

Peripheral blood mononuclear cells (PBMCS) may be used fresh or following cryopreservation (e.g. at −190° C.). DNA may be prepared from PBMCs using standard techniques for use in detection of HIV proviral DNA.

Any suitable HIV primer oligonucleotide(s) may be used in PCR to detect HIV provirus.

In a preferred, nonlimiting embodiment of the invention, cryopreserved (−190° C.) PBMC may be treated with a lysis buffer (for example, 0.45 percent Tween-20, 10 mM Tris HCl pH 8.0, 2.5 mM $MgCl_2$, 50 mM KCl, and 0.1 mg/ml proteinase K) for about two hours at 56° C. and then heat inactivated at 95° C. for 10 minutes. Approximately 1 μg of DNA (20 μl of the PBMC lysate) may be used in the initial PCR amplification with primers A (5'-TTCCCATTAGTCCTATT-3')(SEQ ID NO:8) and NE1 (5'-TCATTGACAGTCCAGCT-3')(SEQ ID NO:7) with reaction conditions as set forth in Larder et al., 1991, AIDS 5:137–144 to generate a 768 bp region of the HIV pol gene.

5.3 PCR ASSAY FOR MUTATION AT CODON 215 OF HIV REVERSE TRANSCRIPTASE

To analyze the changes in codon 215 of the HIV pol gene, a "double" or "nested" PCR procedure was performed using the primers, reagents, and reaction conditions described by Larder et al., 1991, AIDS 5:137–144. Five μl of the 768 bp product generated by PCR with primers A (5'-TTCCCATTAGTCCTATT-3')(SEQ ID NO:8) and NE1 (5'-TCATTGACAGTCCAGCT-3')(SEQ ID NO:7) and either plasma HIV RNA or PBMC DNA may be used in a second series of nested PCR amplifications using primers that detect wild-type sequence or sequence mutated at codon 215. In preferred, non-limiting embodiments of the invention, the following primers may be used: to detect wild-type sequence primers B (5'-GGATGGAAAGGATCACC-3')(SEQ ID NO:9) and 3W (3'-TGGTGTGGTCTGTTTTTTGTA-5')(SEQ ID NO:10) and to detect mutants at codon 215, primers B (supra) and 3M (3'-AAGTGTGGTCTGTTTTTTGTA-5')(SEQ ID NO:11). PCR may then be performed as follows. About 1 μl of template may be used per PCR reaction in 100 μl containing 25 mM KCl, 50 mM Tris HCl pH 8.3, 0.1 mg/ml bovine serum albumin (BSA), 0.2 mM each of DATP, dGTP, dCTP and dTTP, 0.25 μl of each oligonucleotide primer, and 1.5 mM $MgCl_2$. Reaction mixtures may be heated at 100° C. for two minutes prior to addition of Taq DNA polymerase (2.5 U, Perkin-Elmer Cetus, Connecticut), overlaid with 100 μl of light mineral oil, and subjected to 30 cycles consisting of a denaturation step (1 minute, 94° C.), primer annealing (30 seconds, 45° C.) and DNA synthesis (30 seconds, 72° C.) using, for example, a Perkin Elmer Cetus DNA thermal cycler. Ten μl of PCR product from each set of "nested" PCR reactions may then be analyzed to determine the presence and intensity of the products. For example, PCR reactions may be analyzed on a 3.0 percent agarose gel with ethidium bromide staining; a portion of a patient sample subjected to "nested" PCR using primers B and 3W may be run in a lane next to another portion of the same patient sample subjected to "nested" PCR using primers B and 3M. A 210 bp PCR product would be expected; if the patient sample contained HIV RT having the codon 215 mutation, the lane carrying primer B/3M PCR product should exhibit a band that is more intense than any corresponding band in the primer B/3W lane. If the patient sample contained only wild type HIV RT, the band in the primer B/3W lane should be more intense than any corresponding band in the primer B/3M lane. Alternatively, if the patient sample contained a mixture of wild type and mutant HIV RT, bands of similar intensities should be in both lanes. If a sample yielded product with wild-type and mutant primers, the second PCR step may be repeated with serial dilutions of the first round PCR (at dilutions of 1:20, 1:400, and 1:8000); if a mixture of wild type and mutant is still present after serial dilutions, the sample is considered a mixture of wild-type and mutant sequences at the codon of interest.

5.4 PCR ASSAY FOR MUTATION OF CODON 74 OF HIV REVERSE TRANSCRIPTASE

To ascertain the genetic sequence at codon 74, 5 μl of product from the first PCR (using primers A and NE1) may be amplified in a second PCR with primers X2 (5'-AACAATGGCCATTGACAGA-3')(SEQ ID NO:4) and 74WT (wildtype) or X2 and 74M (mutant). The second PCR is a variation of the method described supra using primer X2 instead of primer A. The PCR mixture contained 25 mM Tris HCl (pH 8.3), 50 mM KCl, 1.5 mM $MgCl_2$, 2.5 U Amplitaq DNA polymerase, 250 ng of primer X2 and 250 ng of either primer 74WT or 74M. The reactions were amplified for 30 cycles at 94° C. for 60 sec, 45° C. for 30 sec, and 70° C. for 1 min to generate a 178 bp product.

PCR products were analyzed on 3% agarose gels and visualized by ethidium bromide staining. Samples which yielded product (210-bp for codon 215, 178-bp for codon 74) with the wildtype primers were considered to have a wildtype sequence. Samples which yielded product with the mutant primers were considered to have a mutation at the codon of interest. The product of the first PCR was diluted 1:20 (0.25 μl) and the second PCR was repeated whenever product was initially detected with both wildtype and mutant primers. If product was still detected with both wildtype and mutant primers following dilution, samples were considered to have a mixture of mutant and wildtype forms. For purposes of analysis, HIV-1 strains with either a mutant sequence or a mixture of sequences at a specific codon were considered mutant.

DNA sequencing: A nested PCR assay was also used to obtain DNA segments for sequencing. The first round PCR primers consisted of A' and NE1' [16] which resulted in the amplification of an ≈800 bp fragment of the pol gene. The second round PCR primers were pol1 (SEQ ID NO:12) {5'TGTAAAACGACGGCCAGTGTTAAACAATGGCCATTGATTGACAG3', bp 2609–2630} and pol2 (SEQ ID NO:13) {5'GCAGGAAACAGCTATGACCACAGTGGAGCTGTC3'(SEQ ID NO:14), bp 3287–3309} which contained the M13 forward and reverse primer binding site (underlined) at their 5' ends. This PCR amplified an ≈700 bp gene fragment encompassing codons 28–247 of HIV-1 pol. Second-round PCR products were run on agarose gels and the amplified fragment was excised and purified by centrifugation through Spin-ex columns (Costar). Following precipitation, DNA was sequenced directly using dye-labeled M13 forward and reverse primers on a model 370A DNA Sequencer (Applied Biosystems, Inc., Foster City, Calif.). All sequences were proofread manually.

5.5 UTILITY OF THE INVENTION

The present invention relates to methods of monitoring, via PCR, the clinical progression of HIV infection in patients receiving antiretroviral therapy. Techniques described in Sections 5.1 through 5.4 supra, may be used as set forth below.

In one particular embodiment, the present invention provides for a method of evaluating the effectiveness of antiretroviral therapy of a patient comprising (i)collecting a plasma sample from an HIV-infected patient who is being treated with an antiretroviral agent; (ii) amplifying the HIV-encoding nucleic acid in the plasma sample using HIV primers in about 30 to 40 cycles of PCR; and (iii) testing for the presence of HIV sequence in the product of the PCR; in which the absence of detectable HIV sequence correlates positively with the conclusion that the antiretroviral agent is therapeutically effective and the presence of detectable HIV sequence correlates positively with the conclusion that the antiretroviral agent is therapeutically ineffective. In further, related, embodiments, the presence of detectable HIV sequence correlates positively with an absolute CD4 count of less than 200 cells/mm$^3$, and the absence of detectable HIV sequence correlates positively with a CD4 count greater than 200 cells/mm$^3$. The phrase "correlates positively," as used herein, indicates that a particular result renders a particular conclusion more likely than other conclusions.

In another particular embodiment, the present invention provides for a method of evaluating the effectiveness of antiretroviral therapy of a patient comprising (i) collecting a plasma sample from an HIV-infected patient who is being treated with an antiretroviral agent; (ii) amplifying the HIV-encoding nucleic acid in the plasma sample using HIV primers in about 30 to 40 cycles of PCR; and (iii) measuring the HIV RNA copy number using the product of the PCR, in which an HIV RNA copy number greater than about 500 correlates positively with the conclusion that the antiretroviral agent is therapeutically ineffective, and an HIV RNA copy number less than about 200 correlates positively with the conclusion that the antiretroviral agent is therapeutically effective.

In a further embodiment, the present invention provides for a method of evaluating the effectiveness of antiretroviral therapy of a patient comprising (i) collecting one pre-treatment plasma sample from an HIV-infected patient who is about to be treated with an antiretroviral agent; (ii) collecting a post-treatment plasma sample from the HIV-infected patient after the patient has been treated with the antiretroviral agent; (iii) amplifying the HIV-encoding nucleic acid in the pre-treatment and post-treatment plasma samples using HIV primers in a number of cycles of PCR sufficient to linearly amplify the HIV-encoding nucleic acid to detectable levels, preferably in about 30 to 40 cycles of PCR; (iv) measuring the HIV RNA copy number using the products of the PCRs of step (iii); and (v) comparing the HIV RNA copy number in pre-treatment and post-treatment plasma samples, in which a ratio of HIV RNA copy number in pre-treatment and post-treatment plasma samples of greater than about 4 to 1 or even 10 to 1 correlates positively with the conclusion that the antiretroviral agent is therapeutically effective.

In additional embodiments of the invention, PCR assay may be used to detect mutations at codon 215 of HIV RT which correlate with resistance to antiretroviral therapy and which precede immunologic decline by 6–12 months. Accordingly, the present invention provides for a method of evaluating the effectiveness of antiretroviral therapy of a patient comprising (i) collecting a plasma sample from an HIV-infected patient who is being treated with an antiretroviral agent; and (ii) determining (for example, using "nested" PCR) whether the plasma sample comprises nucleic acid encoding HIV RT having a mutation at codon 215, in which the presence of the mutation correlates positively with immunologic decline of the patient within a six to twelve month period. Under such circumstances, the HIV virus infecting the patient has become, via the mutation, resistant to the antiretroviral agent. It therefore maybe desirable after detecting the mutation, to either increase the dosage of antiretroviral agent, change to another antiretroviral agent, or add one or more additional antiretroviral agents to the patient's therapeutic regimen. For example, if the patient was being treated with zidovudine (AZT) when the mutation arose, the patient's therapeutic regimen may desirably be altered, within about a six to twelve month period of the mutation's occurrence, by either (i) changing to a different antiretroviral agent, such as dideoxyinosine (ddI) and stopping AZT treatment; or (ii) increasing the dosage of AZT; or (iii) adding another antiretroviral agent, such as ddi,to the patient's therapeutic regimen. The effectiveness of the modification in therapy may be evaluated, as set forth above, by monitoring the HIV RNA copy number. A decrease in HIV RNA copy number correlates positively with the effectiveness of a treatment regimen.

Because the mutation at the 215 codon appears first in plasma HIV RNA and later in PBMC proviral DNA, once the mutation is detected in proviral DNA, the treatment regimen is desirably modified with haste in order to avoid immune decline. Accordingly, the present invention provides for a method of evaluating the effectiveness of antiretroviral therapy of a patient comprising (i) collecting PBMC from an HIV-infected patient who is being treated with an antiretroviral agent; and (ii) determining whether the PBMC comprise proviral HIV DNA which comprises a mutation at codon 215, in which the presence of the mutation correlates positively with immunologic decline of the patient within a 4–11 month period (because, as discussed in Section 7, infra, a mutation in serum HIV RNA was found to precede the mutation in proviral DNA by 1–8 months). Once the mutation is detected in proviral DNA, immune decline becomes even more imminent, and alteration of the patient's therapeutic regimen is desirable.

When immune decline is heralded by the increase in HIV RNA copy number and/or the presence of the mutation at codon 215, in addition to altering the patient's antiretroviral therapy, it may also be desirable to treat the patient prophylactically for opportunistic infections, using antifungal, antibiotic, and/or antiparasitic medications.

Antiretroviral agent, as used herein, includes any known antiretroviral agent including, but not limited to, dideoxynucleosides. In preferred embodiments of the invention the antiretroviral agent is AZT. Resistance to certain antiretroviral agents, including AZT, is associated with the mutation at codon 215. Resistance to other antiretroviral agents, such as ddI, is associated with a mutation at codon 74. The present invention provides for analogous techniques in which the effectiveness of antiretroviral therapy is monitored by determining whether plasma HIV RNA or PBMC contain a mutation at codon 74 of HIV RT, in which a mutation at that locus augurs immunological decline and warrants a modification of antiretroviral therapy.

One preferred, non-limiting, specific embodiment of the invention is as follows: A method of evaluating the effectiveness of AZT therapy of a patient comprising (i) collecting a plasma sample from an HIV-infected patient who is being treated with AZT; (ii) amplifying the HIV-encoding RNA in the plasma sample by converting the RNA to cDNA and amplifying HIV sequences using HIV primers in a number of cycles of PCR sufficient to linearly amplify the HIV-encoding nucleic acid to detectable levels, preferably in about 30 to 40 cycles of PCR; and (iii) testing for the presence of HIV sequence in the product of the PCR, in which the absence of detectable HIV sequence correlates positively with the conclusion that AZT is herapeutically effective and the presence of detectable HIV sequence correlates positively with the conclusion that AZT is therapeutically ineffective. In most preferred embodiments, the HIV primers used comprise NE1 (supra), SK38 and/or SK39 (supra) or X2 and 74WT or 74M, and/or the presence of HIV sequence is detected using an enzyme-linked assay (e.g. a horseradish peroxidase based assay). Similar embodiments in which the HIV copy number is measured are also provided for.

Another preferred, non-limiting, specific embodiment of the invention is as follows: A method of evaluating the effectiveness of AZT therapy of a patient comprising (i)

collecting a plasma sample from an HIV-infected patient who is being treated with AZT; (ii) amplifying the HIV-encoding RNA in the plasma sample by converting the RNA to cDNA and amplifying HIV sequences using HIV primers that result in a PCR product that comprises that portion of the RT gene that contains the 215 codon or the 74 codon (e.g. primers A and NE1, supra), or both 215 and 74; (iii) performing "nested" PCR using primers that result in PCR products that reflect the presence of 215 wild type (e.g. primers B and 3W, supra) or mutant codons (e.g. primers B and 3M, supra), or 74 wild type (e.g. primers X2 and 74WT) and mutant codons (e.g. primers X2 and 74M); and (iv) determining, via the products of "nested" PCR, the presence or absence of a mutation at codon 215 or 74 or both of the HIV RT, in which the presence of the mutation correlates positively with immunologic decline of the patient within a six to twelve month period. An analogous method may be used in which the patient sample is PBMC, and the presence of a mutation in proviral DNA is determined.

The presence of the codon 215 mutation indicates that the effectiveness of monotherapy with AZT is likely to decline either in the presence or the absence of the codon 74 mutation. Combination therapy with AZT or a switch to other drugs is generally indicated. Similarly, the presence of the codon 74 mutation indicates that monotherapy with didanosine is likely to decline in effectiveness, and combination therapy, e.g. with didanosine and AZT, or treatment with drugs other than didanosine is generally indicated.

The present invention also provides a kit for detection of mutations at codons 215 or 74 or both.

The kit comprises a first pair of PCR primers which bind outside the region of codon 215 or 74 and therefore may be used to amplify a DNA fragment containing 215 or 74 (e.g. primers A and NE1); and at least two pairs of second round primers which may be used to amplify selectively 215 wild type (e.g. B and 3W) and 215 mutant (e.g. B and 3M) sequences, or 74 wild type (e.g. X2 and 74WT) and 74 mutant (e.g. X2 and 74M) sequences. Optionally the kit may include all four pairs of second primers. Similar primers may be readily chosen by those skilled in the art; the first pair of primers need only amplify a conveniently-sized DNA fragment containing the codon of interest, and one member of the second pair of primers should bind to the codon of interest, preferably having its 3' terminus at the codon of interest in order to maximize the probability of a perfect match resulting in amplification. Optionally the kit may include instructions for interpretation indicting that the presence of the mutant form at the codon of interest correlates with reduced efficacy of a particular antiretroviral therapeutic agent: e.g. presence of the codon 215 mutant indicates reduced efficacy of monotherapy with AZT, and presence of the codon 74 mutant indicates reduced efficacy of monotherapy with ddI.

6. EXAMPLE: REDUCTION IN PLASMA HUMAN IMMUNODEFICIENCY VIRUS RIBONUCLEIC ACID AFTER DIDEOXYNUCLEOSIDE THERAPY AS DETERMINED BY THE POLYMERASE CHAIN REACTION

6.1 MATERIALS AND METHODS

6.1.1 Patients

After informed consent was obtained, whole blood samples were collected by venipuncture in the presence of acid-citrate-dextrose as an anticoagulant. A single plasma sample was collected from 39 HIV antibody-positive subjects who were not receiving antiretroviral therapy at the time of collection and from 33 HIV antibody-positive subjects who were currently on and had received AZT for a minimum of 3 mo.

Two plasma samples were collected from an additional 27 subjects before and 1 month after initiation of dideoxynucleoside therapy. 18 of these subjects received 500 mg/d of AZT orally. Seven subjects received a combination of zidovudine (150–600 mg/d) and 2',3'-dideoxyinosine (ddI) (134–500 mg/d). Two patients received 500 mg/d of ddI alone (see Table I for individual subject characteristics). Finally, nine of these subjects had two plasma samples taken 1–3 wk. before initiating antiretroviral therapy and two plasma samples taken 1 and 2 mo. after commencing therapy. Plasma was separated within 4 h. by centrifugation at 500 g for 10 min. A second centrifugation was performed on the plasma at 500 g for 30 min. to remove any cellular material. 200 $\mu$l of plasma was then mixed with 200 $\mu$l of a solution containing 5M guanidinium thiocyanate, vortexed briefly, and stored at −70° C. until further use. All samples were assayed within 3 mo. of collection. To decrease variance, all specimens to be compared from the same subject were run in the same assay.

6.1.2 Extraction of RNA from Plasma

RNA was extracted from plasma by the method described in Chomczynski et al., 1987, Ann. Biochem. 162:156–159. Briefly, 200 $\mu$l of clarified plasma to which 200 $\mu$l of 5M guanidinium thiocyanate had previously been added was extracted with phenol/chloroform and precipitated with isopropanol. The resulting pellet was then washed in 75% ethanol, dried, and brought up in diethylpyrocarbonate treated, glass distilled water.

6.1.3 Reverse Transcription and Amplification of cDNA

HIV RNA was transcribed to cDNA using Moloney murine leukemia virus reverse transcriptase (Bethesda Research Laboratories, Gaithersburg, Md.) by the method described in Kawasaki, 1990, "In PCR Protocols: A Guide to Methods and Applications" pp. 21–27, M. A. Innis, D. H. Gelfand, J. J. Sninsky, and T. J. White, eds. Academic Press, Berkeley, Calif. Oligomers used for amplification included SK38, SK39, and SK19 (Kellog et al., 1990, "In PCR Protocols: A Guide to Methods and Applications," pp. 337–348, M. A. Innis, D. H. Gelfand, J. J. Sninsky, and T. J. White, eds. Academic Press, Berkeley, Calif.). Biotinylation of SK38 and horseradish peroxidase (HRP) labeling of probe SK19 were prepared as described in Levenson et al., 1990, "In PCR Protocols: A Guide to Methods and Applications," pp. 99–112M. S. Innis, D. H. Gelfand, J. J. Sninsky, and T. J. White, eds. Academic Press, Berkeley, Calif. Amplification of HIV cDNA was carried out as follows: to a 100-$\mu$l reaction mixture was added the cDNA, 50 pmol of primers SK38 and SDK39, 10 mM of each dNTP, 10 mM Tris (pH 8.3), 2.5 mM $MgCl_2$, 50 mM KCl, and 2.5 U of recombiTaq DNA polymerase (Perkin-Elmer Cetus, Norwalk, Conn.). The mixture was then overlaid with 50 $\mu$l of mineral oil. Tubes were placed in a DNA thermal cycler (Perkin-Elmer Cetus) for 30 cycles of amplification with the following program: 95° C./30 s, 55° C./30s, and 72° C./60 s for denaturation, annealing, and extension, respectively. Negative and positive controls which included both high and low copy number HIV RNA and DNA were added at each step.

6.1.4 Enzyme-Linked Affinity Assay

To detect and quantitate PCR product, 96-well microplates (Maxisorp; Nunc, Naperville, Ill.) were coated with 100 $\mu$l of a 0.1 mg/ml solution of avidin (Sigma Chemical Co., St. Louis, Mo.) in 50 mM $Na_2CO_3$ (pH 9.6) overnight at room temperature. Wells were then washed twice with PBS. Wells were then filled with 300 μl of a blocking solution containing 5X Denhardt's solution, 1% gelatin (Sigma), 250 μl/ml sheared herring sperm DNA (Promega Biotec, Madison, Wis.) at least overnight at 4° C. Immediately before use, the blocking solution was aspirated from each well and 5 μl PCR product and 65 μl of a hybridization solution, containing 5X saline sodium phosphate EDTA, 5X Denhardt's solution, and 1 pmol of HRP-labeled SK19 HIV gag specific probe was added to each well. A capture and hybridization reaction was then carried out in the well for 1 h. at 420° C. The 96-well microplate was then placed in a Biomek™ 100 Automated Workstation (Beckman Instruments, Inc., Palo Alto, Calif.) where wells were washed 20 times with BPS containing 0.05% Tween-20. The HRP substrate 0-phenylenediamine (Sigma) was prepared at 0.6 mg/ml in 0.1M citrate buffer (pH 5.5) containing 0.03% hydrogen peroxide. 150 μl of this substrate solution was added to each well. After 10 min. the reaction was stopped with 1N $H_2SO_4$ and the optical density of each well measured at 490 nm by the Biomek 1000. A lower level of positivity had been defined as an absorbance of 0.135. This cutoff value was calculated from the mean absorbance obtained from a group of seronegative samples plus three standard deviations. Copy number from subject samples were determined from the absorbances obtained from a dilution series of an RNA gag gene construct of known copy number described in Holodniy et al., 1991, J. Infect. Dis. 163:862–866. The lower level of sensitivity in this assay was 40 copies of HIV gag gene RNA.

6.1.5 Plasma HIV Culture and P24 Antigen Assay

Quantitative HIV plasma microculture was performed according to the method described in Ho et al., 1989, N. Engl. J. Med. 321:1621–1625. P24 antigen was detected by an antigen capture assay by a method provided by the supplier (Abbott Laboratories, North Chicago, Ill).

6.1.6 Statistical Analysis

Sample optical density was converted to copy number and analyses performed on samples expressed as RNA copy number/200 μl of plasma. A t test of independent samples was used in analysis of subject who did not receive antiretroviral therapy compared to subjects who were receiving AZT. A t test of paired samples was used to analyze paired plasma data and CD4 counts from subjects pre- and post-therapy. All t tests were two tailed. A fisher's exact test or chi square test were used for analysis of proportion where appropriate. Statistical significance was defined as P<0.05.

6.2 RESULTS 72 subjects were evaluated in a cross-sectional study of HIV disease to determine plasma HIV RNA copy number by PCR. The results are presented in FIG. 1. 39 subjects who were not currently receiving antiretroviral therapy and 33 subjects who were receiving AZT were evaluated. Untreated subjects were more likely to have a positive signal than treated subjects (32 of 39 vs. 16 of 33, respectively, P 0.008, chi square). In the 39 subjects who were not currently receiving therapy, the mean plasma HIV RNA copy number was 690±360 (mean±SEM) per 200 μl of plasma, while the 33 subjects who had been receiving AZT therapy had a mean copy number of 134±219 (P<0.05). Mean CD4 count for each group was 316±45 and 300±37, respectively (P=NS).

Subgroups were then analyzed with respect to CD4 count. Among those with <200 CD4 cells, untreated subjects were more likely to have positive signal than treated subjects (18 of 19 vs. 9 of 14, P<0.04, Fisher's exact test). Among those with >200 CD4 cells, 14 of 20 untreated subjects vs. 7 of 19 treated subjects had a detectable signal (P=NS, Fisher's exact test). Untreated subjects with CD4 count <200/mm$^3$ had a mean RNA copy number of 1,369±707 and means CD4 count of 73±17; untreated subjects with CD4>200/mm$^3$ had a mean RNA copy of 44±10 and means CD4 count of 547±45; treated subjects with CD4 counts <200/mm$^3$ had a mean RNA copy number of 295±5 and mean CD4 count of 115±13; and treated subjects with CD4 counts >200/mm$^3$ had calculated mean RNA copy number of 16±5 (which is below the level of detection of this assay and would be interpreted as negative) and mean CD4 count of 437+41.

27 additional subjects were then evaluated before and 1 mo after initiation of dideoxynucleoside therapy. Clinical parameters of the subjects are presented in Table I. PCR results are presented in FIG. 2. Results show that plasma HIV RNA copy number fell from 540±175 to 77±35 after therapy (P<0.05, paired t test). Mean CD4 count increased from 399±24 to 442±25 after 4 wk of therapy (P<0.006, paired t test).

TABLE 1

Clinical Parameters and PCR Analysis of Plasma HIV RNA from 27 Patients

| Patient No. | Antiviral treatment | Pre/post CD4 | Pre/post HIV RNA |
|---|---|---|---|
| 1 | AZT‡ | 647/561 | 106/90 |
| 2 | AZT | 541/651 | 130/0 |
| 3 | AZT | 840/874 | 550/0 |
| 4 | AZT | 432/462 | 100/77 |
| 5 | AZT | 379/415 | 87/57 |
| 6 | AZT | 428/408 | 40/42 |
| 7 | AZT | 422/345 | 94/94 |
| 8 | AZT | 420/402 | 0/0 |
| 9 | AZT | 432/532 | 93/65 |
| 10 | AZT | 430/430 | 105/52 |
| 11 | AZT | 429/404 | 123/50 |
| 12 | ddI + AZT# | 280/220 | 526/0 |
| 13 | AZT | 323/320 | 78/45 |
| 14 | AZT | 320/456 | 95/95 |
| 15 | AZT | 353/387 | 301/0 |
| 16 | ddI + AZT# | 309/399 | 300/0 |
| 17 | ddI + AZT# | 337/398 | 260/0 |
| 18 | ddI‖ | 328/310 | 966/0 |
| 19 | ddI + AZT¶ | 383/491 | 245/0 |
| 20 | AZT | 404/413 | 0/0 |
| 21 | AZT | 270/450 | 958/72 |
| 22 | ddI + AZT¶ | 292/344 | 60/0 |
| 23 | AZT | 320/295 | 2769/437 |
| 24 | ddI‖ | 222/370 | 3944/0 |
| 25 | AZT | 568/732 | 2014/925 |
| 26 | DDI + AZT** | 367/473 | 217/0 |
| 27 | DDI + AZT** | 310/399 | 439/0 |

*Remote history of AZT use.
‡AZT dose 500 mg/d unless otherwise stated.
#AZT 300 mg/d + ddI 334 mg/d.
‖ddI 500 mg/d.
¶AZT 600 mg/d + ddI 500 mg/d.
**AZT 150 mg/d + ddI 134 mg/d.

Finally, 9 of the 27 subjects had two samples taken before initiation of therapy and two samples taken 1 and 2 months after commencing therapy. The results are presented in FIG. 3. When two pretherapy time points were analyzed for constancy of signal, results show that mean copy number for each pretherapy time point was 945+377 and 643±392.

Two subjects had a second pretherapy sample which was negative. When both pretherapy copy number values were compared to posttherapy values, plasma HIV RNA copy number fell from 794±274 to <40 (which is below the lower level of detection in this assay) after 1 and 2 mo of therapy (P<0.05, paired t test). Mean CD4 count increased from 314±165 to 378±25 (P<0.05, paired t test).

Plasma culture was performed on fresh material obtained from the initial pretreatment sample for 23 of 27 of these patients. Only 7 of 23 were plasma virus positive by culture (from 1 to 100 tissue culture infective does/ml). All 23 of these patients were positive by PCR (>40 copies/200 $\mu$l). In addition, a p24 antigen test was performed on all 27 pretreatment samples. Only 2 of 27 had detectable p24 antigen present (>30 pg/ml).

6.3 DISCUSSION

The results presented here demonstrate that plasma HIV RNA can be detected and quantified by copy number in the majority of patients infected with HIV. In addition, plasma HIV RNA copy number may be used as a marker of circulating HIV viral load to assess treatment effect of antiretroviral compounds including dideoxynucleoside compounds. We initially conducted a survey to determine whether treatment or degree of immunologic impairment, based on CD4 count, affected plasma HIV RNA copy number. Untreated patients as a group had higher copy numbers than treated patients. Untreated patients with <200 CD4 cells/mm$^3$ had a higher mean copy number than patients with >200 CD4 cells/MM$^3$. Likewise, treated patients with <200 CD4 cells/MM$^3$/had higher copy numbers than patients with >200 CD4 cells/mm$^3$, indicating that patients with more advanced HIV disease have higher circulating copy numbers than asymptomatic patients, and that the antiretroviral benefit seen in patients with higher CD4 counts may be waning.

To assess the short-term impact of antiretroviral therapy on patients, 27 patients were evaluated before and 1 mo after initiation of AZT, ddI, or combination therapy. As CD4 counts increased after 1 mo of therapy, HIV RNA copy number fell significantly. However, the response of individual subjects was variable. 16 of 27 subjects had a marked decrease in copy number and 11 of 27 did not. Because the majority of subjects received AZT alone, it was not possible to assess any differences between AZT, ddI, or combination regimens.

Finally, nine subjects had two baseline time points taken in the 3 wk before treatment, followed by two monthly samples posttreatment. Pretreatment signal was constant in 7 of 9 subjects, and 2 subjects had discordant samples, i.e., one was positive and one was negative. This could be related to real changes in circulating HIV RNA, or introduced during sample collection, handling, or the assay. However, pretherapy and posttherapy samples were run in the same assay and so were subject to all of the same reaction conditions. When sample positivity was considered in relation to therapy, 16 of 18 pretherapy samples had a positive signal vs. 0 of 18 posttherapy samples ($P<0.001$, chi square) showing suppression of HIV RNA copy number with treatment.

Currently there is no standard method to assess circulating viral load in all HIV-infected patients. Plasma viremia, measured by quantitative microculture, can identify and quantify infectious virus in 50–100% of patients, principally those with advanced stages of HIV disease, low CD4 counts, and p24 antigenemia (Ho et al., 1989, N. Engl. J. Med. 321:1621–1625; Coombs et al., 1989, J. Virol. Methods. 26:23–21; Ehrnst et al., 1988, N. Engl. J. Med. 324:961–964). Many patients with >200 CD4 cells/mm$^3$ do not have detectable infectious plasma viremia. This may be due to an absence of circulating infectious virus, virus which is neutralized by specific antibody, or the insensitivity of culture techniques. The results presented here indicate that the majority of patients with >200 CD4 cells/mm$^3$ do not have plasma p24 antigen or infectious virus detectable by culture techniques. In the studies described herein, it appears that virus undetectable by culture methods was detectable by PCR methods.

Attempts have been made to assess HIV viral load in patients by molecular techniques, mainly by quantitative PCR of HIV proviral DNA in circulating mononuclear cells or cell-free virion-associated RNA in plasma. Published data suggest that the number of cells infected with HIV increases with advancing disease and that HIV proviral DNA content increases as well. We and others have shown a decrease in HIV proviral DNA with dideoxynucleoside therapy over time (Aoki et al., 1990, AIDS Res. Hum. Retroviruses 6:1331–1339). This was not the case in another published small series (McElrath et al., 1991, J. Clin. Invest. 87:27–30).

We have shown that HIV RNA could be quantified in serum and that copy number increased with disease progression (Holodniy et al., 1991, J. Infect. Dis. 163:862–866). Plasma HIV RNA has been shown to be present before and after seroconversion with quantitative decreases occurring after seroconversion (Hewlett et al., 1988, J. Clin. Immunoassay 11:161–164). The recent report by Daar et al. (Daar et al., 1991, N. Engl. J. Med. 324:961–964), showed a decrease in both plasma viremia and proviral DNA from PBMC, coinciding with seroconversion after acute infection. In one report, plasma HIV RNA levels fell with passive immunoglobulin therapy, suggesting a therapy-based response in circulating HIV RNA load (Karpas et al., 1990, Proc. Natl. Acad. Sci. USA 87:7613–7617). Ottman and colleagues have been successful in detecting HIV RNA in plasma from 95% of patients evaluated (Ottman et al., 1991, J. Virol. Methods 31:273–284). They also studied a group of patients who were receiving AZT to determine whether there was any therapeutic impact on HIV RNA signal. 24 of 25 patients who were receiving AZT had detectable signal. However, methodological differences in that study vs. the present study may have contributed to the differences noted between them. First, Ottman et al. used an ultracentrifugation step to sediment virus, enhancing virion-associated RNA recovery. Second, 40 cycles of amplification after reverse transcription were performed, which would certainly increase the sensitivity of such an assay to successfully detect HIV RNA in virtually all patients. Although sensitivity is increased with increased cycle number, thus detecting signal in virtually all patients, the ability to show the quantitative changes demonstrated here with 30 cycles of amplification is lost.

We have previously shown in serum that quantitative serum cultures were negative in the majority of patients with >200 CD4 cells/mm$^3$ (Holodniy et al., 1991, J. Infect. Dis. 163:862–866). In the current study, 23 plasma samples were evaluated by culture and PCR. All had detectable plasma HIV RNA by PCR<but only seven were plasma HIV-culture positive. Other published experience comparing plasma HIV culture and PCR of HIV RNA from plasma is lacking. Ottman et al. tested only two patients, both of whom were positive in both assays. Coyle et al. reported that 14 of 20 patients had positive plasma cultures and 12 of 20 patients had detectable HIV RNA in plasma, but no information was given regarding concordance or discordance of samples (Coyle et al., 1990, Clin. Res. 38:778A (Abstr.)).

The type of plasma sample and method of processing and storage were found to be very important. The type of anticoagulant used for sample collection can affect detection of plasma RNA. We have previously shown that plasma collected in the present of heparin does not allow detection of signal because of an inhibitory effect of heparin on gene amplification (Holodniy et al., 1991, J. Clin. Microbiol. 29:676–679). Although Coyle et al. (1990, Clin. Res. 38:778a (Abstr.)) found detectable signal from plasma collected in the presence of herapin, an ultracentrifugation step preceding RNA analysis lead to removal of most of the heparin from the enzyme-mediated assay system. However, no comparison experiments among anticoagulants were performed to demonstrate any attenuation of signal obtained in the presence of heparin.

Because of our concern for RNA degradation during specimen storage and freeze thawing, we decided to store fresh plasma at −70° C. in the presence of guanidinium and process samples within 3 mo of collection. Samples were stored in guanidinium for RNAase inhibition. Preliminary data from our laboratory would suggest that plasma HIV RNA signal decays with time in the absence of this RNA stabilizer.

In summary, we have shown that plasma HIV RNA copy number can be quantitated by PCR and does decrease with dideoxynucleoside therapy. The nonisotopic, microplate-based format presented here makes it possible to process multiple patient samples with replicates in a single amplification and assay run.

7. EXAMPLE: RELATIONSHIP OF A MUTATION IN THE HIV REVERSE TRANSCRIPTASE GENE TO DECLINE IN CD4 LYMPHOCYTE NUMBERS IN LONG TERM AZT RECIPIENTS

7.1 MATERIALS AND METHODS 7.1.1 Study Population

Cryopreserved PBMC and serum from 40 participants in AIDS Clinical Trial Group (ACTG) protocols 019 (30 patients) and 016 (10 patients) at Stanford University Medical Center AIDS Clinical Trial Unit were used in this study. Patients at enrollment in these studies were AZT naive, had >200 CD4 cells/μl and had few (016) or no symptoms (019) referable to HIV infection. They were subsequently treated with AZT for 2 to 4 years. The most common dosage was 500 mg per day. Approximately one third of patients received either 1200 mg or 1500 mg per day during the initial part of their therapy, but were changed to 500 mg per day when lower doses were found to be as effective but less toxic than higher doses (Fischl et al., 1990, N. Engl. J. Med. 323:1009–1014; Volberding et al., 1990, N. Engl. J. Med. 322:941–949). All samples were obtained from the patients while they were on the protocols and thus no patient developed on AIDS defining diagnosis.

7.1.2 CD4 Cell Counts

CD4 cell counts were obtained approximately every three months on each patient. All counts were performed at Stanford's ACTG-qualified cytofluorometry lab. Samples were stained with monoclonal antibodies to CD3, CD4, and CD8. The absolute CD4 count was calculated by multiplying the percent CD4 by the total lymphocyte count.

7.1.3 PBMC Preparation

Cryopreserved (−190° C.) PBMC were treated with a lysis buffer (0.45% Tween-20, 10 mM Tris HCl pH 8.0, 2.5 mM $MgCl_2$, 50 mM KCl, and 0.1 mg/ml proteinase K) for 2 hours at 56° C. and then heat inactivated at 95° C. for 10 min. Approximately lug of DNA (20 μl of the PBMC lysate) was used in the initial PCR amplification with primers A(5'-TTCCCATTAGTCCTATT-3')(SEQ ID NO:8) and NE1 (5'-TCATTGACAGTCCAGCT-3')(SEQ ID NO:17) with reaction conditions as described in Larder et al., 1991, AIDS 5:137–144 to generate a 768 bp region of the HIV pol gene.

7.1.4 Serum HIV RNA Preparation

Cryopreserved (−70° C.) serum was thawed and then 350 μl of sera was added to 350 μl of solution D (Chomczynski et al., 1987, Anal. Biochem. 162:156–159) (guanidinium thiocyanate+2-mercaptoethanol) and vortexed. RNA was then extracted with phenol and chloroform and precipitated with ethanol as described in Chomczynski et al., 1987, Anal. Biochem. 162:156–15918. HIV RNA was then reverse transcribed to cDNA by using 500 ng of primer NEI and 200 units of murine leukemia virus (MuLV) reverse transcriptase (Bethesda Research Labs) in 10 μl of amplification buffer (25 mmol/L KCl, 50 mmol/L Tris HCl Ph 8.3, 0.1 mg/ml bovine serum albumin, 1.45 mmol/L each of dATP, dGTP, dCTP and dTTP, 1.5 mmol/L $MgCl_2$, 2.5 units of RNasin (Promega)) for 10 min at room temperature, then 30 min at 42° C. followed by heat inactivation at 95° C. for 5 min. This cDNA was then amplified by PCR using 250 ng of primer A in a reaction mixture (100 μl) containing the same buffer as above with 0.25 mmol/L of each dNTP and 2.5 units of AmpliTaq DNA polymerase (Perkin-Elmer Cetus). This reaction mixture underwent 30 cycles of 94° C. for 1 min, 45° C. for 1 min and 72° C. for 2 min to generate a 768 bp region of the HIV pol gene.

7.1.5 PCR Analysis of HIV Reverse Transcriptase Gene

To analyze the changes in codon 215 of the HIV pol gene, a "double" PCR procedure was performed using the primers, reagents, and reaction conditions described in Larder et al., 1991, AIDS 5:137–144. Five μl of the 768 bp product generated by PCR with primers A and NE1 was used in a second series of nested PCR amplifications using primer B and 3W to determine if a wild type sequence was present, or B and 3M to determine if a mutant sequence was present (primer sequences as et forth supra and in Larder et al., 1991, AIDS 5:137–144). Samples were run with negative, positive and reaction mixture controls. Ten μl of PCR product from each of the second set of PCR reactions were analyzed on a 3.0% agarose gel with ethidium bromide staining. PCR products were considered to have a mutant or wild type sequence by the method described by Boucher et al. (1990, Lancet 336:585–590; 1992, J. Infect. Dis. 165:105–110) and Larder et al., 1991, AIDS 5:137–144: a sample was considered to contain the wild type sequence at codon 215 if amplification with the primers B and 3W resulted in a 210 bp PCR product of highest intensity; a sample was considered to contain a mutant sequence at codon 215 if amplification with the primers B and 3M resulted in a 210 bp PCR product of highest intensity. The sample was considered to have a mixture of wild type and mutant sequences if amplification occurred with both primers 3M and 3W resulting in PCR products of similar intensity. If a mixture was detected by PCR then that sample was included in the mutant group in our statistical analysis.

7.1.6 AZT Sensitivity Assay

Patient PBMC were cocultured with mitogen-stimulated PBMC from healthy HIV-seronegative donors. Supernatants from these cultures were collected and frozen when the HIV P24 antigen concentration exceeded 10,000 pg/ml. 30–100 $TCID_{50}$ (50% tissue culture infectious dose) of virus stock was used to infect one million donor PBMC pretreated with different concentrations of AZT (0.0 μM, 0.005 μM, 0.05 μM, 0.5 μM, 5.0 μM). After 7 days, P24 antigen was measured in the cell free supernatant from the cultures with and without zidovudine. The concentration of AZT required to inhibit P24 production by 90% ($IC_{90}$) as compared to the drug free cultures was determined by nonlinear regression analysis (Chou et al., 1984, Adv. Enzyme Regulation 22:27–55). In this assay, the $IC_{90}$s from AZT-naive patients ranged from 0.002 μM to 0.038 μM AZT.

7.1.7 Statistical Analysis

All comparisons between the patients with mutant and wild type strains were performed using the student's t-test. The calculations on the IC90s determined by the zidovudine sensitive assay were performed using the $\log_{10}$ transformed $IC_{90}$ (i.e., geometric means were used rather than arithmetic means).

7.2 RESULTS 7.2.1 PCR Analysis of codon 215 in PBMC

Proviral DNA was detected by nested PCR in the PBMC of 38 of 40 patients after a mean 34 month treatment period. The two patients in whom proviral DNA could not be detected had high CD4 counts at the time their PBMC were analyzed (729 and 676 cells/μl). PCR amplification of the PBMC from 17 of 38 patients (45%) yielded a 210 bp product with the mutant primer, indicating the presence of a mutation at codon 215 (Thr to Tyr or Phe). The PBMC from 21 of 38 patients (55%) demonstrated amplification product only with the wild type primer (a 210 bp product) indicating the presence of Thr at codon 215.

The mean length of therapy and starting CD4 counts for the two groups were similar (Table 2). However, the 17 patients with a mutation at codon 215 of HIV RT in PBMC proviral DNA had a 50% decrease in their absolute CD4 count between the time they began therapy (378 cells/μl) and the end of the study (189 cells/μl). The 21 patients with a wild type sequence at codon 215 experienced a mean 11% increase in their absolute CD4 count between the time they began therapy (397 cells/μl) and the end of the study (424 cells/μl). The post-treatment CD4 percentages of the two groups of patients were also significantly different (25% in patients with wild-type sequence vs 14% in patients with a mutation in RT at codon 215)(Table 2). The CD4 counts at each time point for each patient are shown in FIGS. 4A and 4B.

TABLE 2

CORRELATION OF PATIENT CD4 COUNT CHANGES WITH PCR ANALYSIS OF CODON 215 OF HIV REVERSE TRANSCRIPTASE IN PBMC

| | Wildtype | Mutant | p |
|---|---|---|---|
| Number of patients | 21 | 17 | |
| Months of AZT | 33 ± 8 | 35 ± 7 | 0.4 |
| Starting CD4 measurements | | | |
| Absolute CD4 (cells/μl) | 397 ± 124 | 378 ± 96 | >0.5 |
| CD4 % | 26 ± 8 | 25 ± 6 | >0.5 |
| CD4 measurements at a time of PCR analysis | | | |
| Absolute CD4 (cell/μl) | 424 ± 210 | 189 ± 98 | <0.0001 |
| CD4 % | 25 ± 9 | 14 ± 6 | 0.0001 |

7.2.2 PCR Analysis of Codon 215 in HIV RNA from Serum

Serial PBMC samples from earlier time points were available on 8/40 patients; however, serial serum samples from earlier time points were available on 37/40 patients. In these 37 patients, 135 serum samples were tested for the presence of a codon 215 mutation. In 87% of these samples (117), reverse transcribed cDNA could be detected by PCR. Fifteen of the 18 sera that were negative by PCR had been previously subjected to multiple freeze-thaws and therefore could be falsely negative. As all patients were AZT-naive, they were assumed to be wild type at codon 215 at the start of AZT therapy.

Twenty-six of the 37 patients developed a mutation in their HIV RNA. This included the 16 who were also mutant in their PBMC at the end of the study period (FIG. 5A), and ten patients who were wild type in their PBMC but mutant in serum HIV RNA at the end of the study period (FIG. 5B). The time preceding the occurrence of the 215 mutation in their serum ranged from 2 to 44 months of therapy. Among these 26 patients, the mean CD4 count at the start of therapy was 398±139 cells/μl and their mean CD4 count at the time of first detection of a codon 215 mutation in their serum was 444±206 cells/μl. Nineteen of the 26 patients with a codon 215 mutation in their serum had follow-up CD4 counts at least 12 months after the mutation was first detected. In these 19 patients, there was a mean decrease of 100±116 CD4 cells/μl (25% decline) at six months and a mean decrease of 170±121 CD4 cells/μl (40% decline) at 12 months.

The 11 patients who remained wild type in their serum over the entire 34 month period of zidovudine therapy had an increase of 7±92 CD4 cells/μl (2% increase), (FIG. 5C). The mean CD4 count at the start of therapy for the patients who later developed a mutant in their serum was 398±139 cells/μl and this was not significantly different than the starting CD4 counts for those patients who remained wild type (397±115 cells/μl, p>0.5). The average length of therapy for both groups was 34 months.

7.2.3 Serum Virus Compared to PBMC Provirus

At the final evaluation of the 38 patients after a mean 34 months of zidovudine, 11 patients were wild type in both serum and PBMC, 17 were mutant in both serum and PBMC, and 10 patients had a mutation in their serum but remained wild type in their PBMC FIG. 6. Eight of the 17 patients with a mutation in proviral DNA at the end of the study period had at least one PBMC sample available from an earlier time point. In these eight patients, a mutation in serum HIV RNA preceded the mutation in proviral DNA by 1–8 months. The findings in these 8 patients and in the 10 patients who were wild type in their PBMC but mutant in their serum shows that detection of the serum mutation precedes detection of the mutation in PBMC. In no instance, did a mutation in patient's PBMC precede its appearance in serum.

7.2.4 AZT Sensitivity Results Determined by Cell Culture

In vitro AZT susceptibility testing was performed on 17 of 38 patients using a different aliquot of the same post-treatment PBMC that were used for the PCR analysis. The geometric mean of the $IC_{90}$s of eight patients with the wild type form at 215 was 0.04 μm AZT (range: 0.02–0.28 μm); the geometric mean $IC_{90}$ of nine patients with a mutation at codon 215 was 0.41 μm AZT (range: 0.03–8.0 μM; p=0.002).

7.3 DISCUSSION

As an increasing number of HIV infected individuals are offered early treatment with AZT, the significance of drug resistant virus has become an important question. In the present study we found a strong correlation between the presence of a mutation at codon 215, which is linked to AZT resistance and an accelerated decline in CD4 cell number. The patients we studied all began taking AZT when their CD4 cell numbers were relatively high and before the onset of AIDS. We observed that the 17 patients with a mutation at codon 215 in proviral DNA in their PBMC experienced a mean 50% decrease in their CD4 count between the time that they began therapy and the time that their cells were analyzed for mutations. The 21 patients who were wild type at codon 215 in their proviral DNA at the end of treatment experienced a mean 11% increase in their CD4 count during the same time period.

Patient cells were only available during the last year of the study. However, by extracting and reverse transcribing HIV RNA from patient's serum specimens we were able to detect codon 215 mutation at earlier time points. The patients in our study with and without a mutation in serum HIV had similar starting CD4 counts (397±115 vs. 398±139, p>0.5) and similar lengths of therapy (34 months in both groups). Yet we found that those patients who develop a mutation in HIV RNA had a subsequent 40% decline in their CD4 cells over the next 12 months. The patients who remained wild type in their serum had a 2% increase in their CD4 cells over 34 months of therapy.

These results show that genetic changes in the virus which confer drug resistance can be rapidly determined directly from patient PBMC and HIV RNA in patients serum using a nested PCR procedure. By using PCR we were able to detect viral nucleic acid in 90% of PBMC samples and 87% of serum samples. Techniques which require culturing HIV from PBMC or serum may select HIV subpopulations with greater tropism for certain cells (Kusumi et al., 1992, J. Virol. 66:875–885; Meyerhans et al., 1989, Cell 58:901–910). This may complicate the analysis of the clinical significance of AZT resistance detected by phenotypic assays.

Earlier clinical studies focused on AZT resistance in patients with initially low CD4 cell counts or who were at high likelihood of disease progression. Furthermore, these studies tested HIV isolates which had been passaged in culture. In contrast, in this study we did not select patients at high likelihood for disease progression but instead we included all patients who remained on AZT for at least 2 years and who had high CD4 counts at the beginning of the study; codon 215 mutations in serum virus occurred early in treatment. The mean CD4 count at the first appearance of the mutation was higher than the CD4 count at the start of therapy (444 vs. 398 cells/$\mu$l). This suggests that mutation of the reverse transcriptase gene is not dependent upon low $CD4^+$ T cells. On the other hand, we also found that a large percentage of patients remained wild type at codon 215 and phenotypically sensitive to AZT despite almost 3 years of therapy. This may be because our patients were less advanced in their disease or that by using PCR instead of coculture we were able to include patients whose virus might not have grown in culture. These results also suggest that the PBMC may not be the initial source of mutant virus, as evidenced in 18 of our patients where the serum HIV RNA mutation preceded that in PBMC by many months. The source of the mutant HIV detected in serum may be cells in lymphatic, central nervous system or reticuloendothial sites.

The significance of specific mutations in the RT gene with respect to AZT resistance has been defined in patient isolates as well as through molecular cloning experiments (Larder et al., 1989, Science 246:1155–1158; Larder et al., 1991, AIDS 5:137–144; Kellam et al., 1992, 89:1934–1938; St. Clair et al., supra). Of the four mutations first reported to be associated with AZT resistance (codons 67, 70, 215, 219), the mutation at codon 215 has been shown to be the most commonly occurring and to have the greatest impact on susceptibility. This impact on AZT susceptibility will vary depending on whether or not additional mutations are present (Larder et al., 1989, Science 246:1155–1158; Larder et al., 1991, AIDS 5:137–144; Kellam et al., 1992, 89:1934–1938; St. Clair et al., 1991, Science 253:1557–1559; Richman et al., 1991, J. Infect. Dis. 164:1075–1081; Boucher et al., 1992, J. Infect. Dis. 165:105–110). Recent sequencing studies of clinical isolates suggest that there are additional mutations in the RT gene that may contribute to AZT resistance (Japour et al., 1991, Proc. Natl. Acad. Sci. 88:3092–96; Kellam et al, 1992, Proc. Natl. Acad. Sci. USA 89:1934–1938; St. Clair et al., 1991, Science 253:1557–1559). However, the occurrence of the two consecutive nucleotide changes necessary for the amino acid change at codon 215 may be the most important requirement for the development of resistance (Kellam et al., 1992, Proc. Natl. Acad. Sci. USA 89:1934–1938; Richman et al., 1991, J. Infect. Dis. 164:1075–1081; Boucher et al., 1992, J. Infect. Dis. 165:105–110). In this study, a subset of 17 patients were tested using a cell culture assay which confirmed that the viruses with a mutation at codon 215 had reduced susceptibility to AZT.

The patients with resistant or sensitive virus in our study had similar CD4 counts at the start of AZT therapy and received AZT for a similar period of time. Therefore, the development of resistance and a mutation at codon 215 could not be attributed to any known pretreatment characteristic. None of our patients developed AIDS during our study period and the patients who developed a mutation in their serum HIV RT did so at a relatively high CD4 count. Thus, advanced stage of HIV disease could not explain why some patients developed a mutation while others did not. Additional characteristics of the patient or virus may explain why one HIV strain develops a mutation and another does not. It has been stated that syncytium-inducing, T-cell tropic isolates in HIV-infected individuals contribute to the CD4 cell decline (Tersmette et al., 1989, Lancet 1:983–985). If an HIV isolate can maintain a high level of replicative events despite the presence of AZT, this virus would have a much greater likelihood of mutation. Treatment with AZT may select both syncytium-inducing and drug resistant virus. Selection of more virulent HIV population under prolonged AZT pressure may explain why some patients experienced a CD4 cell decline in the months after the RT mutation arose.

The present report shows a strong association between the presence of a HIV RT mutation and declining CD4 counts in AZT treated patients. Furthermore, it demonstrates that a HIV mutation known to cause AZT resistance can be detected prior to a decline in CD4 cell number.

8. EXAMPLE: MEASUREMENTS OF CODON 74 AND 215 MUTATIONS IN HIV PATIENTS SWITCHED FROM AZT TO ddI MONOTHERAPY

8.1.1 METHODS 8.1.1 Patients

Sixth-four patients infected with HIV enrolled in the following three protocols at Stanford University Medical Center: 1) 8 patients enrolled in Stanford University/San Mateo County Didanosine Protocol (Katzenstein et al., 1994, J. Infect. Dis. 169:416–419) an open-labeled study involving patients who had received zidovudine (Retrovir; Burroughs Wellcome, Research Triangle Park, N.C.) for more than 16 months who were switched to didanosine; 2) 33 patients enrolled in AIDS Clinical Trial Group Protocols (2) 116b/117 study who had tolerated zidovudine for at least 16 weeks and were than switched to didanosine; and 3) 23 patients enrolled in AIDS Clinical Trial Group Protocol 118 study who were intolerant to zidovudine and who had been switched to didanosine. The baseline $CD4^+$ T-cell counts of the patients ranged from 6 to 400 $CD4^+$ T cells/$mm^3$ (median, 105 $CD4^+$ cells/$mm^3$), and patients had either AIDS, AIDS-related complex, or were asymptomatic. No patient had an active opportunistic infection at the time of enrollment into the study, and patients received Pneumocystis carinii prophylaxis as defined by each protocol and were allowed to continue suppressive therapy for previously diagnosed opportunistic infections (Kahn et al., supra).

Patients received didanosine (Videx; Bristol Laboratories, Princeton, N.J.) monotherapy at one of three possible dosages: 200 mg/d (6 patients), 500 mg/d (31 patients), or 750 mg/d (27 patients). Serial serum samples were saved at week 0, 2, 8, 12, 16, 24, 32, 40, and 48; at these same time points. $CD4^+$ T-cell determinations were done. All patients were followed until the close of their study or until death.

8.2 REVERSE-TRANSCRIPTASE GENE MUTATIONAL ANALYSIS

Cryopreserved (−70° C.) serum was thawed and 200 μL was ultracentrifuged at 125 000×g for 10 minutes. The resulting pellet was dissolved in 400 μL of 5M guanidinium thiocyanate. Serum HIV RNA was then extracted as previously described (20–22). Extracted viral RNA using 500 ng of primer 35-NE1 (Larder et al., 1994, In: Persing DH, ed. Diagnostic Molecular Microbiology) and 200 units of murine leukemia virus reverse transcriptase (Bethesda Research Laboratories, Gaithersburg, Md.) with reaction conditions and controls as previously described (Kozal et al., supra; Shafer et al., 1994, J. Infect. Dis. 169:722–729). The complementary DNA was amplified by PCR using 250 ng of primer 35-A with the reaction conditions described by Larder and Boucher and colleagues (Larder et al., 1991, AIDS 5:137–144). For selective PCR, 5 μL of the 805 basepair product from the first PCR was used in the second series of reactions. Primers 3W (wild type), 3M (mutant), and B were used to determine the sequence at codon 215; primers X2 and 74WT (wild type) and 74M (mutant) (St. Clair et al., 1991, Science 253:1557–1559) were used to determine the sequence at codon 74. Master mix, negative, wild-type, and mutant sequenced controls were amplified in each sample run. Nonreversed transcribed control samples subjected to the PCR procedure yielded negative results, and patient RNA samples treated with DNAase yielded identical results to patient RNA samples using our extraction procedure, validating that the reverse transcriptase-PCR product was the result of HIV RNA and not DNA. The purity of the extracted RNA using the guanidinium thiocyanate-phenol-chloroform extraction technique has been previously reported by Chomczynski and Sacchi (Chomczynski et al., 1987, Anal. Biochem. 162:156–159). Fifteen HIV isolates that had been tested in our laboratory by nested PCR for the codon 74 and 215 mutations were also sequenced and confirmed the presence or absence of these mutations.

Products from PCR were analyzed on a 3% agarose gel with ethidium bromide staining. All samples from the start had been blinded by a code number, and thus the evaluator who scored the PCR product had no knowledge of sample origin (that is, the corresponding patient). Samples yielding a product with only the wild-type primers were considered wild type. Samples that yielded product with only the mutant primers were considered mutant. If a sample yielded product with wild-type and mutant primers, the second PCR step was repeated with serial dilutions of the first round PCR (at dilutions of 1:20, 1:400, and 1:8000); if a mixture of wild type and mutant was still present after serial dilutions, the sample was considered a mixture of wild-type and mutant sequences at the codon of interest. Samples with a mixture of wild-type and mutant sequences at the codon were included in the mutant group in our statistical analysis.

8.3 SERUM HIV RNA PREPARATION FOR VIRUS BURDEN

Duplicate serum samples were ultracentrifuged, and the pellet was purified by phenol-chloroform extraction and alcohol precipitation, as previously described for plasma (Winters et al., 1993, J. Clin. Microbiol. 31:2960–2966). Polymerase chain reaction quantification of viral RNA was done using reverse-transcriptase PCR, and the PCR product was detected using a nonisotopic enzyme-hybridization assay, as previously described (Winters et al., 1992, PCR Methods Appl. 1:257–262). Results were then expressed as HIV RNA copies per milliliter of serum.

8.4 HIV BIOLOGICAL PHENOTYPE

For the 25 patients for whom cryopreserved peripheral blood mononuclear cells were available, viral stocks were created from these mononuclear cells by cocultivation with peripheral blood mononuclear cells from patients who were seronegative from HIV. Viral stock supernatant (the tissue culture infective $dose_{50}$ was about 2000), 200 μL, was cultured with 8 mL of MT-2 cells ($0.5\times10^6$ cells/mL) in duplicate. Cultures were maintained for three weeks and were examined for syncytia twice a week, as described by Koot and colleagues (Koot et al., 1992, AIDS 6:49–54).

8.5 $CD4^+$ CELL COUNTS $CD4^+$ cell counts were done at weeks 0, 2, 4, 8, 12, 16, 24, 32, 40, and 48.

8.6 STATISTICAL ANALYSIS

A two-sided t-test was used to compare changes in virus burden between patient groups. A standard one-sample, two-sided Wilcoxon test was used to compare differences in the change of slopes of $CD4^+$ T cells (slopes of $CD4^+$ cells before the mutation compared with slopes of $CD4^+$ cells after the mutation) for patients developing a mutation at codon 74. The slope difference test analysis pertained to the slope difference statistic, defined to be the difference in fitted slope of the $CD4^+$ counts after compared with before the mutation at codon 74. Thirty-four of 38 patients in the mutation group had sufficient data to allow computation of the slope difference statistic.

We compared the slope difference statistic values for the 34 mutants with the corresponding values from the wild-type group in order to see if they were more negative in the mutant group. This is not possible directly because the wild-type group by definition has no mutation time from which to define "before" and "after." Instead, artificial slope difference values were constructed as follows: 1) a random participant was chosen from the 25 in the wild-type group; 2) a random mutation time was chosen from the 38 such times in the mutation group; and 3) if the mutation time was less than the last observation time for the randomly selected participant, then the wild-type slope difference value was set equal to the slope difference for that participant using that mutation time to define before and after. If the mutation time was not less, then we started over at step 1). One hundred and fifty-two values were constructed in this way. A two-sample, two-sided Wilcoxon test was used to show that the 34 mutant values were statistically significantly more negative than the 152 wild-type values. A two-sided chi-squared test was used to analyze the differences in the frequency of the mutations in the patients receiving different dosages of didanosine.

8.7 RESULTS

8.7.1 Baseline characteristics

Sixty-four patients who had received zidovudine and were switched to didanosine monotherapy were evaluated for the presence of codon 74 and 215 reverse-transcriptase mutations at serial time points (base line through week 48). The mean (±SD) $CD4^+$ T-cell count at the start of didanosine for all patients was 129±88 $CD4^+$ cells/$mm^3$ (median, 105 $CD4^+$ cells/$mm^3$). The mean (± SD) time on didanosine monotherapy for all patients was 10.5±5.7 months (median, 9 months).

8.7.2 Reverse-Transcriptase Mutations

At baseline, 54 of 64 (84%) patients had a mutation at codon 215, whereas 0 of 64 (0%) patients had a mutation at codon 74. By week 24 of didanosine monotherapy, 36 of 64 (56%) patients had developed a mutation at codon 74. At week 24, the number of patients who had a mutation at codon 215 in their serum HIV RNA had decreased from 84% to 59% (38 of 64); 16 patients previously mutant at codon 215 in serum HIV RNA now only had wild-type sequences (a 25% difference, 95% lower CI, 15%; P<0.0001, the Fischer exact test). The rate of mutation at codon 74 and codon 215 at weeks 0, 8, 12, 16, and 24 is shown Table 3.

A greater proportion of patients receiving the highest dose of didanosine developed the codon 74 mutation, but this difference was not significant; thus, 54% (20 of 37) of patients receiving 200 mg/d or 500 mg/d of didanosine developed the mutation, whereas 70% (19 of 27) of patients receiving 750 mg/d of didanosine developed the mutation (P=0.18, two-sided chi-squared test). As shown in Table 3, the most common genotype in the 64 patients at the final time point for each patient before they went off study was that of a mutation at codon 74 with a persisting codon 215 mutation (74MUT/215MUT), followed by patients remaining wild type at codon 74 and wild type at codon 215 (74 WT/215 WT), and then patients with combinations of wild type and mutant genotypes (74 MUT/215 WT and 74 WT/215MUT). No significant difference was found between patients with syncytium-inducing and nonsyncytium-inducing isolates with respect to the presence of the codon 74 mutation in HIV serum RNA: in patients with syncytium-inducing isolates, 67% (6 of 9) had the codon 74 mutation compared with 56% (9 of 16) patients with nonsyncytium-inducing isolates.

TABLE 3

INCIDENCE OF A DIDANOSINE RESISTANCE MUTATION AT CODON 74 AND A ZIDOVUDINE RESISTANCE MUTATION AT CODON 215 OF THE HIV REVERSE-TRANSCRIPTASE GENE IN 64 PATIENTS WHO SWITCHED FROM ZIDOVUDINE TO DIDANOSINE*

| | Week | | | | |
|---|---|---|---|---|---|
| Variable | 0 | 8 | 12 | 16 | 24 |
| Codon 74, n (%) | | | | | |
| Wild type | 64(100) | 56(88) | 49(77) | 45(70) | 28(44) |
| Mixture** | 0(0) | 8(12) | 7(11) | 9(14) | 9(14) |
| Mutant | 0(0) | 0(0) | 8(12) | 10(16) | 27(42) |
| Codon 215, n (%) | | | | | |
| Wild type | 10(16) | 20(31) | 23(36) | 26(41) | 26(41) |
| Mixture** | 12(19) | 3(5) | 3(5) | 2(3) | 1(2) |
| Mutant | 42(65) | 41(64) | 38(59) | 36(56) | 37(58) |

*Percentage of patients with the combination of genotype (at codon 74 and 215) at the final time they went off study: codon 74 wild type/codon 215 wild type, 23%; codon 74 wild type/codon 215 mutant, 16%; codon 74 mutant/codon 215 wild type, 17%; codon 74 mutant/codon 215 mutant, 44%.

**Patients with a mixture of wild type and mutant codon sequences.

8.8 $CD4^+$ T-CELL CHANGES RELATED TO THE HIV REVERSE-TRANSCRIPTASE GENOTYPE

Changes in patients $CD4^+$ T-cell counts were analyzed to determine the relation to the codon 74 mutation. The starting $CD4^+$ T-cell counts were not significantly different for the 25 patients who 35 remained wild type at codon 74 compared with the 39 patients who developed a mutation at codon 74 (mean [±SD], 134±102 $CD4^+$ cells/$mm^3$ compared with 125±78 $CD4^+$ cells/$mm^3$; P>0.5). Almost all patients (63 of 64) had follow-up $CD4^+$ T cells available. The patients who had mutations as early as 8 to 16 weeks after starting didanosine had lower starting $CD4^+$ T-cell counts than the patients who did not have mutations until week 24 or after (mean [±SD], 85±58 $CD4^+$ cells/$mm^3$ compared with 152±79 $CD4^+$ cells/$mm^3$; P<0.01).

FIG. 9 shows the pattern of $CD4^+$ T-cell changes before and after the appearance of the codon 74 mutation in the 38 patients receiving didanosine who developed this mutation. Most of the patients (34 of 38) who developed the codon 74 mutation had $CD4^+$ T-cell values available after developing the mutation; 4 patients developed the codon 74 mutation at the last evaluable time point before they stopped taking didanosine and had no further $CD4^+$ T-cell values. The slopes of the $CD4^+$ T-cell changes were significantly more negative after the codon 74 mutation compared with before the mutation (a median greater decline of −1.54 $CD4^+$ cells/wk; CI, −2.68 to −0.71; P<0.002). These slope values were also compared with randomized slope differences generated by superimposing a mutation time from the mutant group on a randomly chosen case history from the codon 74 wild-type group, 152 values were compared. Patients with the mutation had greater decreases in their $CD4^+$ T cells after developing the mutation (significantly more negative slopes) than did patients who remained wild type during the same time period (P<0.001).

8.9 HIV GENOTYPE RELATED TO CHANGES IN SERUM VIRUS BURDEN

Serum virus burden determined by quantitative PCR was done at week 0 and week 24 for 58 of 64 patients (Table 4). The remaining 6 patients did not have enough serum left after mutational analysis for quantitative testing. Patients who developed the codon 74 mutation had a higher mean virus burden at initiation of didanosine (83 000 HIV RNA copies/mL serum (CI, 51 900 to 133 000 copies/mL serum) compared with patients who remained wild type at codon 74 (50 100 HIV RNA copies/mL serum; CI, 24 200 to 103 000), a 1.6-fold greater virus burden, although the difference was not significant (CI, 0.7 to 3.94; P=0.20). Patients who developed a codon 74 mutation had a greater serum virus burden after 24 weeks of didanosine than did patients who remained wild type (a 2.7-fold greater virus burden; CI, 1.26 to 5.89 P=0.01). Although patients with the codon 74 mutant had a greater increase in their serum virus burden during the first 24 weeks of didanosine than did patients remaining wild type at codon 74, the magnitude of the difference was not significant (Table 4).

TABLE 4

CHANGES IN SERUM VIRUS BURDEN IN PATIENTS RECEIVING DIDANOSINE MONOTHERAPY RELATED TO THE GENOTYPE AT CODON 74 OF THE HIV REVERSE-TRANSCRIPTASE GENE

| Variable | Patients Whose Genotypes Remained Wild type | Patients Whose Genotypes Became Mutant | P Value | Fold Difference (95% CI) |
|---|---|---|---|---|
| Patients, n | 26 | 32 | | |
| Week 0, mean HIV RNA copies/mL serum (95% CI) | 50100 (24200 to 103000) | 83000 (51900 to 133000) | 0.2* | 1.66 (0.70 to 3.94) |
| Week 24, mean HIV RNA copies/mL serum (95% CI) | 82400 (42000 to 161000) | 225000 (151000 to 334000) | 0.01* | 2.71 (1.26 to 5.89) |
| Fold increase in virus burden between week 0 to 24 | 1.65 (0.95 to 2.89) | 271 (1.73 to 4.24) | 0.26* | |

*Two-sided two sample t-test on the log of the values.
**Two-sided t-test on the log differences between week 0 to 24 for patients who had wild type genotypes compared with those who had mutant genotypes.

8.9.1 Discussion

It has been established that five HIV reverse-transcriptase gene mutations (at codons 41, 67, 70, 215, and 219) can confer resistance to zidovudine (Larder et al., 1989, Science 246:1155–1158; Kellam et al., 1992, Proc. Natl. Acad. Sci. USA 89:1934–1938). Data from several groups (Richman et al., 1991, J. Infect. Dis. 164:1075–1081; Boucher et al., 1992, J. Infect. Dis. 165:105–110) indicate the relative frequency and pattern of development of these mutations in patients receiving zidovudine monotherapy. It has become important to investigate the frequency of didanosine resistance because more patients who have taken zidovudine are being switched to didanosine. Previous work has established that the mutation at codon 74 appears to confer the greater degree of resistance to didanosine (a 5- to 26-fold decrease in susceptibility), and this mutation has been shown to provide a replication advantage to HIV-1 compared with that of wild-type viruses in vivo and in vivo (cell culture experiments) in the presence of didanosine (Shirasaka et al., 1993, Proc. Natl. Acad. Sci. USA 90:562–566; Eron et al., 1993, Antimicrob. Agents Chemother. 37:1480–1487).

Because of these reports, we investigated the frequency and pattern of development of the codon 74 mutation in 64 patients who had previously taken zidovudine and who had been switched to didanosine monotherapy. The codon 74 mutation was detected in serum HIV RNA from these patients as early as 8 weeks after starting didanosine; by week 24 of didanosine treatment, 56% of the patients had developed a mutation at codon 74. All of the patients previous zidovudine therapy; on entry into the study, 84% of them had a mutation at codon 215 (a mutation known to confer a 16-fold decrease in zidovudine susceptibility). After 24 weeks of didanosine treatment, the number of patients with a codon 215 mutation had decreased to 59% (that is, 16 patients who had had mutant sequences at codon 215 in their serum HIV RNA were now wild type at this codon). This transformation from mutant to wild type may have been the result of a reversion of the reverse-transcriptase gene mutation back to the wild-type sequence or a more likely possibility is that once the pressure of zidovudine was removed, there was reexpression and release of the wild-type virus into the serum from the large reservoir of different viral quasispecies infecting a given patient.

Zidovudine resistance occurs more rapidly in patients with decreased $CD4^+$ T-cell levels (Richman et al., 1990, AIDS 3:743–746), and the mutations that cause zidovudine resistance are associated with a greater virus burden. Both of these findings for zidovudine resistance also apply to codon 74 mutations for patients receiving didanosine. Patients with mutations at codon 74 after just 8 to 16 weeks of didanosine had decreased starting levels $CD4^+$ T cells when compared with patients who did not develop a codon 74 mutation until week 24 or later. All patients who developed the codon 74 mutation tended to have a higher serum virus burden at the start of therapy and had a greater serum virus burden (statistically significant) after 24 weeks of didanosine therapy than did the patients who were wild type at codon 74. This finding may reflect that a patient with a greater virus burden is likely to generate mutations faster given the chance for more replicative events than does a patient with a low virus burden.

The most common genotype found in the 64 patients during the 48 weeks of didanosine treatment was the combination of a codon 74 mutation with a preexisting zidovudine resistance mutation at codon 215 (in 44% of patients). This subgroup of patients also had the highest serum virus burden after 24 weeks of didanosine therapy (mean about 275 400 HIV RNA copies/mL serum). The high frequency of a HIV genotype with codon 74 and 215 mutations suggests that although this combination would not be favored by the virus in the presence of zidovudine because it can restore zidovudine susceptibility, it is readily selected for in patients receiving didanosine monotherapy. The selection of this combination by the virus and its association with a high virus burden may be related to the findings of Eron and colleagues and St. Clair and colleagues. These researchers using site-directed mutagenesis showed that the presence of zidovudine resistance mutations in the HIV reverse transcriptase in combination with the codon 74 mutation may confer an even greater degree of didanosine resistance that does the codon 74 mutation alone. Thus, viruses with this combination of mutations are likely to have a selection advantage in a patient receiving didanosine monotherapy. In patients with advanced disease who were receiving didanosine monotherapy, those with the codon 74 mutation, were found to have a statistically significant greater decrease in their $CD4^+$ T cells after the development of the codon 74 mutation when compared with patients who remained wild type at codon 74 during the same time period. Thus, a temporal relation appears to exist between the development of the codon 74 mutation in the serum HIV RNA of these patients and a more severe subsequent decrease in $CD4^+$ T cells when compared with patients who remain wild type at this codon while receiving didanosine monotherapy.

In patients infected with HIV, zidovudine resistance (Tudor-Williams et al., supra; Mayers et al., 1993, In: Conference on Human Retroviruses and Related Infections) and HIV resistance nonnucleoside reverse-transcriptase inhibitors (Richan, D. D., 1993, Antimicrob. Agents Chemother. 37:1207–1213; Richman, D.D., 1992, In: Program Abstracts of VIII International Conference on AIDS, Amsterdam, Netherlands, p. 3576; Davey et al., 1993, Proc. Natl. Acad. Sci. USA, 90:5608–5612; Kappes et al., 1992, In: VII International Conference on AIDS, Amsterdam, Netherlands, Abstr.) have been shown to be associated with and predictive of decrease in $CD4^+$ T cells and disease progression. Despite the size of this study and the advanced disease stage of the patients at the start of didanosine therapy, an association was found between the development of the didanosine resistance mutation at codon 74 in the serum HIV RNA of these patients and a subsequent accelerated decrease of $CD4^+$ T cells when compared with patients without the mutation who were receiving didanosine monotherapy. In addition, patients with the mutation were found to have a greater serum virus burden (statistically significant) than the patients without the mutation after 24 weeks of didanosine.

All publications, patents, and patent applications cited herein are hereby incorporated by reference to the extent necessary to understand the invention.

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
(A) LENGTH: 28 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 1:

ATAATCCACC TATCCCAGTA GGAGAAAT 28

(2) INFORMATION FOR SEQ ID NO: 2:

(i) SEQUENCE CHARACTERISTICS:
(A) LENGTH: 28 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 2:

TTTGGTCCTT GTCTTATGTC CAGAATGC 28

(2) INFORMATION FOR SEQ ID NO: 3:

(i) SEQUENCE CHARACTERISTICS:
(A) LENGTH: 41 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 3:

ATCCTGGGAT TAAATAAAAT AGTAAGAATG TATAGCCCTA C 41

(2) INFORMATION FOR SEQ ID NO: 4:

(i) SEQUENCE CHARACTERISTICS:
(A) LENGTH: 19 base pairs
(B) TYPE: nucleic acid
(C) STRANDEDNESS: unknown
(D) TOPOLOGY: unknown (ii) MOLECULE TYPE: DNA (genomic)

-continued (xi) SEQUENCE DESCRIPTION: SEQ ID NO: 4:

AACAATGGCC ATTGACAGA 19

(2) INFORMATION FOR SEQ ID NO: 5:

(i) SEQUENCE CHARACTERISTICS:
(A) LENGTH: 21 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 5:

AAGTTCTCTG AAATCTACTT A 21

(2) INFORMATION FOR SEQ ID NO: 6:

(i) SEQUENCE CHARACTERISTICS:
(A) LENGTH: 21 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 6:

AAGTTCTCTG AAATCTACTT C 21

(2) INFORMATION FOR SEQ ID NO: 7:

(i) SEQUENCE CHARACTERISTICS:
(A) LENGTH: 17 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 7:

TCATTGACAG TCCAGCT 17

(2) INFORMATION FOR SEQ ID NO: 8:

(i) SEQUENCE CHARACTERISTICS:
(A) LENGTH: 17 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 8:

TTCCCATTAG TCCTATT 17

(2) INFORMATION FOR SEQ ID NO: 9:

(i) SEQUENCE CHARACTERISTICS:
(A) LENGTH: 17 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO: 9:

GGATGGAAAG GATCACC 17

-continued

```
(2) INFORMATION FOR SEQ ID NO: 10:

     (i) SEQUENCE CHARACTERISTICS:
          (A) LENGTH: 21 base pairs
          (B) TYPE: nucleic acid
          (C) STRANDEDNESS: unknown
          (D) TOPOLOGY: unknown

    (ii) MOLECULE TYPE: DNA (genomic)

    (xi) SEQUENCE DESCRIPTION: SEQ ID NO: 10:

ATGTTTTTTG TCTGGTGTGG T                                          21


(2) INFORMATION FOR SEQ ID NO: 11:

     (i) SEQUENCE CHARACTERISTICS:
          (A) LENGTH: 21 base pairs
          (B) TYPE: nucleic acid
          (C) STRANDEDNESS: unknown
          (D) TOPOLOGY: unknown

    (ii) MOLECULE TYPE: DNA (genomic)

    (xi) SEQUENCE DESCRIPTION: SEQ ID NO: 11:

ATGTTTTTTG TCTGGTGTGA A                                          21


(2) INFORMATION FOR SEQ ID NO: 12:

     (i) SEQUENCE CHARACTERISTICS:
          (A) LENGTH: 44 base pairs
          (B) TYPE: nucleic acid
          (C) STRANDEDNESS: unknown
          (D) TOPOLOGY: unknown

    (ii) MOLECULE TYPE: DNA (genomic)

    (xi) SEQUENCE DESCRIPTION: SEQ ID NO: 12:

TGTAAAACGA CGGCCAGTGT TAAACAATGG CCATTGATTG ACAG                 44


(2) INFORMATION FOR SEQ ID NO: 13:

     (i) SEQUENCE CHARACTERISTICS:
          (A) LENGTH: 33 base pairs
          (B) TYPE: nucleic acid
          (C) STRANDEDNESS: unknown
          (D) TOPOLOGY: unknown

    (ii) MOLECULE TYPE: DNA (genomic)

    (xi) SEQUENCE DESCRIPTION: SEQ ID NO: 13:

GCAGGAAACA GCTATGACCA CAGTGGAGCT GTC                             33
```

What is claimed is:

1. A method of evaluating the effectiveness of antiretroviral therapy of an HIV-infected patient comprising:

(i) collecting a plasma sample from an HIV-infected patient; and (ii) determining whether the plasma sample comprises nucleic acid encoding HIV reverse transcriptase having a mutation at [codons] *codon* 215 [or 74, or codons 215 and 74], in which the presence of the [mutations] *mutation* correlates positively with an accelerated immunologic decline of said patient compared to patients who do not have the [mutations] *mutation*.

2. The method of claim 1 in which the mutation at codon 215, [74, or 215 and 74 are] *is* determined by a method comprising polymerase chain reaction (PCR).

3. The method of claim 2 which comprises a "nested" polymerase chain reaction.

4. The method of claim 2 which utilizes primer B (5'-GGATGGAAAGGATCACC-3')(SEQ ID NO:9).

5. The method of claim 2 which utilizes primer 3M (3'-AAGTGTGGTCTGTTTTTTGTA-5')(SEQ ID NO:11).

6. The method of claim 2 which utilizes primer 74WT (5'-AAGTTCTCTGAAATCTACTTA-3')(SEQ ID NO:5).

7. The method of claim 2 which utilizes primer 74MUT (5'-AAGTTCTCTGAAATCTACTTC-3')(SEQ ID NO:6).

8. The method of claim 2 which utilizes primer X2 (5'-AACAATGGCCATTGACAGA-3')(SEQ ID NO:4).

9. The method of claim 1 in which the antiretroviral [agent] *therapy being evaluated* comprises zidovudine.

10. The method of claim 1 in which the antiretroviral [agent] *therapy being evaluated* comprises didanosine.

11. The method of claim 2 wherein PCR is repeated for 30 to 40 cycles.

12. The method of claim 11 wherein PCR is repeated for 30–35 cycles.

13. A method of evaluating the effectiveness of antiretroviral therapy of an HIV-infected patient comprising:

(i) collecting PBMC from an HIV-infected patient; and (ii) determining whether the PBMC comprise proviral HIV DNA which comprises a mutation at [codons 74 or] *codon* 215[, or codons 215 and 74,] of the HIV reverse transcriptase gene, in which the presence of the [mutations] *mutation* correlates positively with an accelerated immunologic decline of said patient compared with patients who do not have the [mutations] *mutation*.

14. The method of claim 13 in which the [mutations] *mutation* at [codons 74 or] *codon* 215[, or 215 and 74 are] *is* determined by a method comprising polymerase chain reaction.

15. The method of claim 14 which comprises a nested polymerase chain reaction.

*16. A method of evaluating the effectiveness of antiretroviral therapy of an HIV-infected patient comprising:*

*(i) collecting a plasma sample from an HIV-infected patient; and*

*(ii) determining whether the plasma sample comprises nucleic acid encoding HIV reverse transcriptase having a mutation at codon 74, in which the presence of the mutation correlates positively with an accelerated immunologic decline of said patient compared to patients who do not have the mutation.*

*17. The method of claim 16 in which the mutation at codon 74, is determined by a method comprising polymerase chain reaction (PCR).*

*18. The method of claim 17 which comprises a "nested" polymerase chain reaction.*

*19. The method of claim 17 which utilizes primer B (5'-GGATGGAAAGGATCACC-3')(SEQ ID NO:9).*

*20. The method of claim 17 which utilizes primer 3M (3'-AAGTGTGGTCTGTTTTTTGTA-5')(SEQ ID NO:11).*

*21. The method of claim 17 which utilizes primer 74WT (5'-AAGTTCTCTGAAATCTACTTA-3')(SEQ ID NO:5).*

*22. The method of claim 17 which utilizes primer 74MUT (5'-AAGTTCTCTGAAATCTACTTC-3')(SEQ ID NO:6).*

*23. The method of claim 17 which utilizes primer X2(5'-AACAATGGCCATTGACAGA-3')(SEQ ID NO:4).*

*24. The method of claim 16 in which the antiretroviral therapy being evaluated comprises zidovudine.*

*25. The method of claim 16 in which the antiretroviral therapy being evaluated comprises didanosine.*

*26. The method of claim 17 wherein PCR is repeated for 30 to 40 cycles.*

*27. The method of claim 26 wherein PCR is repeated for 30–35 cycles.*

*28. A method of evaluating the effectiveness of antiretroviral therapy of an HIV-infected patient comprising:*

*(i) collecting a plasma sample from an HIV-infected patient; and*

*(ii) determining whether the plasma sample comprises nucleic acid encoding HIV reverse transcriptase having a mutation at codons 215 and 74, in which the presence of the mutation correlates positively with an accelerated immunologic decline of said patient compared to patients who do not have the mutation.*

*29. The method of claim 28 in which the mutation at codons 215 and 74 is determined by a method comprising polymerase chain reaction (PCR).*

*30. The method of claim 29 which comprises a "nested" polymerase chain reaction.*

*31. The method of claim 29 which utilizes primer B (5'-GGATGGAAAGGATCACC-3')(SEQ ID NO:9).*

*32. The method of claim 29 which utilizes primer 3M (3'-AAGTGTGGTCTGTTTTTTGTA-5')(SEQ ID NO:11).*

*33. The method of claim 29 which utilizes primer 74WT (5'-AAGTTCTCTGAAATCTACTTA-3')(SEQ ID NO:5).*

*34. The method of claim 29 which utilizes primer 74MUT (5'-AAGTTCTCTGAAATCTACTTC-3')(SEQ ID NO:6).*

*35. The method of claim 29 which utilizes primer X2(5'-AACAATGGCCATTGACAGA-3')(SEQ ID NO:4).*

*36. The method of claim 28 in which the antiretroviral therapy being evaluated comprises zidovudine.*

*37. The method of claim 28 in which the antiretroviral therapy being evaluated comprises didanosine.*

*38. The method of claim 29 wherein PCR is repeated for 30 to 40 cycles.*

*39. The method of claim 38 wherein PCR is repeated for 30–35 cycles.*

*40. A method of evaluating the effectiveness of antiretroviral therapy of an HIV-infected patient comprising:*

*(i) collecting PBMC from an HIV-infected patient; and*

*(ii) determining whether the PBMC comprise proviral HIV DNA which comprises a mutation at codon 74 of the HIV reverse transcriptase gene, in which the presence of the mutation correlates positively with an accelerated immunologic decline of said patient compared with patients who do not have the mutation.*

*41. The method of claim 40 in which the mutation at codon 74 is determined by a method comprising polymerase chain reaction.*

*42. The method of claim 41 which comprises a nested polymerase chain reaction.*

*43. A method of evaluating the effectiveness of antiretroviral therapy of an HIV-infected patient comprising:*

*(i) collecting PBMC from an HIV-infected patient; and*

*(ii) determining whether the PBMC comprise proviral HIV DNA which comprises a mutation at codons 215 and 74, of the HIV reverse transcriptase gene, in which the presence of the mutation correlates positively with an accelerated immunologic decline of said patient compared with patients who do not have the mutation.*

*44. The method of claim 43 in which the mutation at codons 215 and 74 is determined by a method comprising polymerase chain reaction.*

*45. The method of claim 44 which comprises a nested polymerase chain reaction.*

* * * * *